United States Patent [19]

Or et al.

[11] Patent Number: 6,046,171
[45] Date of Patent: Apr. 4, 2000

[54] 6,11-BRIDGED ERYTHROMYCIN DERIVATIVES

[75] Inventors: Yat Sun Or, Libertyville, Ill.; George Griesgraber, Eagan, Minn.; Leping Li, Foster City; Daniel T. Chu, Santa Clara, both of Calif.

[73] Assignee: Abbott Laboratories, Abbott Park, Ill.

[21] Appl. No.: 09/158,459

[22] Filed: Sep. 22, 1998

Related U.S. Application Data

[60] Provisional application No. 60/063,712, Oct. 29, 1997.

[51] Int. Cl.⁷ .............................. A61K 31/70; C07H 1/00; C07H 17/08
[52] U.S. Cl. .............................. 514/29; 536/7.2; 536/7.4; 536/18.5
[58] Field of Search .................... 536/7.2, 7.4, 18.5; 514/29

[56] References Cited

U.S. PATENT DOCUMENTS

| | | | |
|---|---|---|---|
| 4,990,602 | 2/1991 | Morimoto et al. | 536/7.4 |
| 5,403,923 | 4/1995 | Kashimura et al. | 536/7.4 |
| 5,444,051 | 8/1995 | Agouridas et al. | 514/29 |
| 5,527,780 | 6/1996 | Agouridas et al. | 514/29 |

FOREIGN PATENT DOCUMENTS

| | | |
|---|---|---|
| WO9710251 | 3/1997 | WIPO . |
| 9717356 | 5/1997 | WIPO . |
| WO9717356 | 5/1997 | WIPO . |

OTHER PUBLICATIONS

Journal of Antibiotics, vol. 37. No. 2 (1984), pp. 187–189, Moritmoto, et al., "Chemical Modification of Erythromycins. I. Synthesis and Antibacterial Activity of 6–O–Methylerythromycins A".

Journal of Antibiotics, vol. 43, No. 3 (1990), pp. 286–292, Moritmoto, et al., "Chemical Modification of Erythromycins. II. Synthesis and Antibacterial Activity of O–Alkl Derivatives of Erythromycin A".

*Primary Examiner*—Elli Peselev
*Attorney, Agent, or Firm*—Mona Anand

[57] ABSTRACT

Novel 6,11-bridged erythromycin compounds and pharmaceutically acceptable salts and esters thereof having antibacterial activity having a formula compositions comprising a therapeutically effective amount of a compound of the invention in combination with a pharmaceutically acceptable carrier, a method for treating bacterial infections by administering to a mammal a pharmaceutical composition containing a therapeutically-effective amount of a compound of the invention, and processes for their preparation.

19 Claims, No Drawings

6,11-BRIDGED ERYTHROMYCIN DERIVATIVES

This application claims the benefit of the Provisional Patent Application, Ser. No. 60/063,712, filed Oct. 29, 1997.

TECHNICAL FIELD

This invention relates to novel semi-synthetic macrolides having antibacterial activity, to pharmaceutical compositions comprising these compounds, and to a medical method of treatment. More particularly, the invention relates to novel 6,11-bridged erythromycin derivatives, methods for preparing them, compositions containing these compounds, and a method of treating bacterial infections with such compositions.

BACKGROUND OF THE INVENTION

Erythromycins A through D, represented by formula (E),

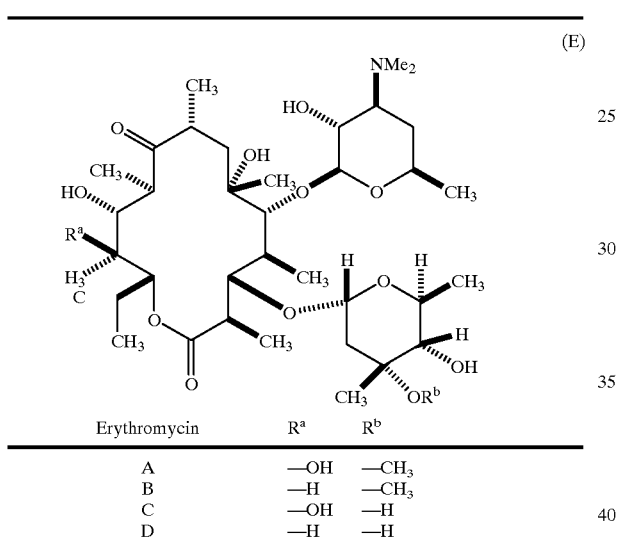

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Morimoto et al. describes the preparation of 6-O-methyl erythromycin A in *J. Antibiotics,* 37:187 (1984). Morimoto et al. further discloses 6-O-alkyl erythromycin A derivatives in *J. Antibiotics,* 43: 286 (1990) and in U.S. Pat. No. 4,990,602.

U.S. Pat. No. 5,444,051 discloses certain 6-O-substituted-3-oxoerythromycin A derivatives. PCT application WO 97/10251, published Mar. 20, 1997, discloses intermediates useful for preparation of 6-O-methyl 3-descladinose erythromycin derivatives.

U.S. Pat. No. 5,403,923 discloses certain tricyclic 6-O-methyl erythromycin A derivatives, and U.S. Pat. No. 5,527,780 discloses certain bicyclic 6-O-methyl-3-oxo erythromycin A derivatives.

PCT application WO 97/17356, published May 15, 1997, discloses tricyclic 6-O-methyl erythromycin A derivatives. Certain intermediates to the present invention are disclosed in U.S. patent application Ser. No. 08/888,350.

SUMMARY OF THE INVENTION.

The present invention provides a novel class of 6,11-bridged erythromycin derivatives which possess antibacterial activity.

In one aspect of the present invention are compounds, or pharmaceutically acceptable salts and esters thereof, having a formula selected from the group consisting of

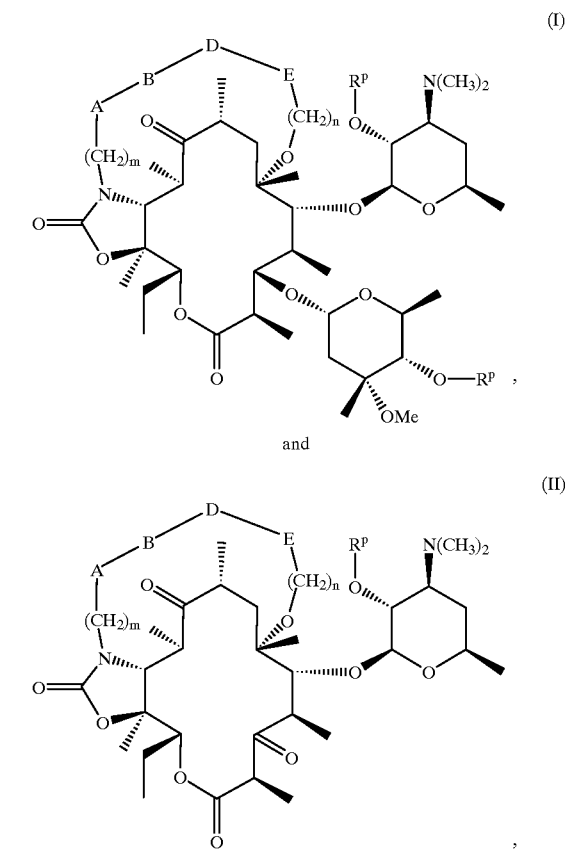

wherein
m is 0, 1, 2, 3, 4, 5, 6 or 7;
n is 0, 1, 2, 3 or 4;
RP is independently hydrogen or a hydroxy protecting group at each occurrence;
A is absent or is selected from the group consisting of
(1) —O—, and
(2) —N(R$^1$)—, wherein R$^1$ is hydrogen or C$_1$–C$_6$-alkyl optionally substituted with aryl or heteroaryl;
B is absent or is selected from the group consisting of
(1) —(CH$_2$)$_q$—, wherein q is 0, 1, 2, 3, 4, 5, or 6,
(2) —C(O)—(CH$_2$)$_q$—,
(3) —C(O)—O—(CH$_2$)$_q$—,
(4) —C(O)—NR$^1$—(CH$_2$)$_q$—, wherein R$^1$ is as defined previously, and (5) —N=CH—(CH$_2$)$_q$—;
(6) —CH(OH)—(CH$_2$)$_q$—, and
(7) —CH(OH)—CH(OH)—(CH$_2$)$_q$—;

D is absent or is selected from the group consisting of
(1) alkenylene,
(2) arylene,
(3) substituted arylene,
(4) heteroarylene,
(5) substituted heteroarylene;
(6) alkenylene-arylene,
(7) arylene-arylene,
(8) substituted arylene-arylene,
(9) heteroarylene-arylene,
(10) substituted heteroarylene-arylene,
(1 1) alkenylene-heteroarylene,
(12) arylene-heteroarylene,
(13) substituted arylene-heteroarylene,
(14) heteroarylene-heteroarylene, and
(15) substituted heteroarylene-heteroarylene;

E is absent or is selected from the group consisting of
(1) —(CH$_2$)$_r$—CH=CH—,
(2) —(CH$_2$)$_r$—O—, wherein r is 0, 1, 2, 3 or 4,
(3) —(CH$_2$)$_r$NR$^1$—CH$_2$—CH(OH)—, wherein R$^1$ is as defined previously,
(4) —(CH$_2$)$_r$—C(O)—O—,
(5) —(CH$_2$)$_r$—N(R$^1$)—,
(6) —(CH$_2$)$_r$O—C(O)—,
(7) —(CH$_2$)$_r$—C(O)—N(R$^1$)—, and
(8) —(CH$_2$)$_r$—N(R$^1$)—C(O)—, with the restrictions that the sum of m+q may not be 0, that the sum of m+n+q+r is an integer from 2 to 7, that when the A and B moieties are both absent then m cannot be 0, that when E is —CH=CH— and the A, B and D moieties are all absent then m cannot be 0, and that B can be —N=CH—(CH$_2$)$_q$— only when A is absent and m is 0.

The present invention also provides pharmaceutical compositions which comprise a therapeutically effective amount of a compound as defined above in combination with a pharmaceutically acceptable carrier.

The invention further relates to a method of treating bacterial infections in a host mammal in need of such treatment comprising administering to a mammal in need of such treatment a therapeutically effective amount of a compound as defined above.

In a further aspect of the present invention, processes are provided for the preparation of 6,11-bridged erythromycin derivatives of Formula (I) above.

DETAILED DESCRIPTION OF THE INVENTION

Definitions

As used throughout this specification and the appended claims, the following terms have the meanings specified.

The terms "C$_1$–C$_3$-alkyl", "C$_1$–C$_6$-alkyl", and "C$_1$–C$_{12}$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of C$_1$–C$_3$-alkyl radicals include methyl, ethyl, propyl and isopropyl, examples of C$_1$–C$_6$-alkyl radicals include, but are not limited to, methyl, ethyl, propyl, isopropyl, n-butyl, tert-butyl, neopentyl and n-hexyl. Examples of C$_1$–C$_{12}$-alkyl radicals include, but are not limited to, all the foregoing examples as well as n-heptyl, n-octyl, n-nonyl, n-decyl, n-undecyl and n-docecyl.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "C$_2$–C$_{12}$-alkenyl" denotes a monovalent group derived from a hydrocarbon moiety containing from two to twelve carbon atoms and having at least one carbon-carbon double bond by the removal of a single hydrogen atom. Alkenyl groups include, for example, ethenyl, propenyl, butenyl, 1-methyl-2-buten-1-yl, and the like.

The term "C$_2$–C$_{12}$-alkenylene" denotes a divalent group derived from a hydrocarbon moiety containing from two to twelve carbon atoms and having at least one carbon-carbon double bond by the removal of two hydrogen atoms. Alkenylene groups include, for example, 1,1-ethenyl, 1,2-propenyl, 1,4-butenyl, 1-methyl-but-1-en-1,4-yl, and the like.

The term "C$_1$–C$_6$-alkoxy" as used herein refers to an C$_1$–C$_6$-alkyl group, as previously defined, attached to the parent molecular moiety through an oxygen atom. Examples of C$_1$–C$_6$-alkoxy, but are not limited to, methoxy, ethoxy, propoxy, iso-propoxy, n-butoxy, tert-butoxy, neo-pentoxy and n-hexoxy.

The term "C$_1$–C$_3$-alkylamino" as used herein refers to one or two C$_1$–C$_3$-alkyl groups, as previously defined, attached to the parent molecular moiety through a nitrogen atom. Examples of C$_1$–C$_3$-alkylamino include, but are not limited to methylamino, dimethylamino, ethylamino, diethylamino, and propylamino.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heteroaryl compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "aryl" as used herein refers to a mono- or bicyclic carbocyclic ring system radical derived from a hydrocarbon moiety containing one or two aromatic rings, respectively, by removal of a single hydrogen atom. Such aryl radicals include, but are not limited to, phenyl, naphthyl, tetrahydronaphthyl, indanyl, indenyl and the like.

The term "arylene" denotes a divalent group derived from an aryl moiety as defined previously by the removal of two hydrogen atoms. Arylene groups include, for example, 1,2-phenyl, 1,3-phenyl, 1,4-phenyl, 1,2-naphthyl, 1,4-naphthyl, 1,6-naphthyl, and the like.

The term "C$_3$–C$_7$-cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, and bicyclo[2.2.1]heptyl.

The terms "halo" and "halogen" as used herein refer to an atom selected from fluorine, chlorine, bromine and iodine.

The term "alkylamino" refers to a group having the structure —NHR' wherein R' is alkyl, as previously defined, Examples of alkylamino include methylamino, ethylamino, iso-propylamino and the like.

The term "dialkylamino" refers to a group having the structure —NR'R" wherein R' and R" are independently selected from alkyl, as previously defined. Additionally, R' and R" taken together may optionally be —(CH$_2$)$_k$— where k is an integer of from 2 to 6. Examples of dialkylamino include, dimethylamino, diethylaminocarbonyl, methylethylamino, piperidino, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "alkoxycarbonyl" represents an ester group; i.e. an alkoxy group, attached to the parent molecular moiety through a carbonyl group such as methoxycarbonyl, ethoxycarbonyl, and the like.

The term "thioalkoxy" refers to an alkyl group as previously defined attached to the parent molecular moiety through a sulfur atom.

The term "carboxaldehyde" as used herein refers to a group of formula —CHO.

The term "carboxy" as used herein refers to a group of formula —CO$_2$H.

The term "carboxamide" as used herein refers to a group of formula —CONHR'R" wherein R' and R" are independently selected from hydrogen or alkyl, or R' and R" taken together may optionally be —(CH$_2$)$_k$— where k is an integer of from 2 to 6.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, and the like.

The term "heteroarylene" denotes a divalent group derived from an heteroaryl moiety as defined previously by the removal of two hydrogen atoms. Heteroarylene groups include, for example, 2,3-pyridyl, 2,4-pyridyl, 2,6-pyridyl, 2,3-quinolyl, 2,4-quinolyl, 2,6-quinolyl, 1,4-isoquinolyl, 1,6-isoquinolyl, and the like.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heteroarylalkyl" as used herein, refers to a heteroaryl group as defined above attached to the parent molecular moiety through an alkylene group wherein the alkylene group is of one to four carbon atoms.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis,* 2nd edition, John Wiley & Sons, New York (1991). Examples of hydroxy-protecting groups include, but are not limited to, methylthiomethyl, tert-dimethylsilyl, tert-butyldiphenylsilyl, ethers such as methoxymethyl, and esters including acetyl benzoyl, and the like.

The term "ketone protecting group", as used herein, refers to an easily removable group which is known in the art to protect a ketone group against undesirable reactions during synthetic procedures and to be selectively removable. The use of ketone-protecting groups is well known in the art for protecting groups against undesirable reactions during a synthetic procedure and many such protecting groups are known, cf., for example, T. H. Greene and P. G. M. Wuts, *Protective Groups in Organic Synthesis.* 2nd edition, John Wiley & Sons, New York (1991). Examples of ketone-protecting groups include, but are not limited to, ketals, oximes, O-substituted oximes for example O-benzyl oxime, O-phenylthiomethyl oxime, 1-isopropoxycyclohexyl oxime, and the like.

The term "oxo" denotes a group wherein two hydrogen atoms on a single carbon atom in an alkyl group as defined above are replaced with a single oxygen atom (i.e. a carbonyl group).

The term "N-protecting group" or "N-protected" as used herein refers to those groups intended to protect an amino group against undesirable reactions during synthetic procedures. N-protecting groups comprise carbamates, amides including those containing hetero aryl groups, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, triphenylmethyl (trityl), t-butyloxycarbonyl (Boc), benzyloxycarbonyl (Cbz), nicotinoyl and the like. Commonly used N-protecting groups are disclosed in T. H. Greene and P. G. M. Wuts, *Protective Groups in Organic Synthesis.* 2nd edition, John Wiley & Sons, New York (1991), which is hereby incorporated by reference.

The term "protected-amino" refers to a amino group protected with a N-protecting group, as defined above, including benzoyl, acetyl, trimethylsilyl, triethylsilyl, methoxymethyl groups, for example.

The term "protected-hydroxy" refers to a hydroxy group protected with a hydroxy protecting group, as defined above, including formyl, acetyl, benzoyl, pivaloyl, phenylsulfonyl, benzyl, triphenylmethyl (trityl), t-butyloxycarbonyl (Boc), and benzyloxycarbonyl (Cbz) groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of*

*Purification*, 4th ed., edited by John A. Riddick et al., Vol. II, in the Techniques of Chemistry Series, John Wiley & Sons, NY, 1986.

The term "substituted aryl" as used herein refers to an aryl group as defined herein substituted by independent replacement of one, two or three of the hydrogen atoms thereon with halo, hydroxy, cyano, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, acylamino, mercapto, nitro, carboxaldehyde, carboxyl, alkoxycarbonyl and carboxamide. In addition, any one substituent may be an aryl, heteroaryl, or heterocycloalkyl group. Also, substituted aryl groups include tetrafluorophenyl and pentafluorophenyl.

The term "substituted arylene" as used herein refers to an arylene group as defined herein substituted by independent replacement of one, two or three of the hydrogen atoms thereon with halo, hydroxy, cyano, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, acylamino, mercapto, nitro, carboxaldehyde, carboxyl, alkoxycarbonyl and carboxamide. In addition, any one substituent may be an aryl, heteroaryl, or heterocycloalkyl group. Also, substituted aryl groups include tetrafluorophenyl and pentafluorophenyl.

The term "substituted heteroaryl" as used herein refers to a heteroaryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "substituted heteroarylene" as used herein refers to a heteroarylene group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Preferred Embodiments

In a first embodiment of the invention is a compound having the formula (I). In a preferred embodiment of formula (I), E is —CH=CH— and n is 1.

In a second embodiment of the invention is a compound having the formula (II). In a preferred embodiment of formula (II), E is —CH=CH— and n is 1.

Representative compounds of the invention are those selected from the group consisting of:

Compound of Formula (I), 2'-$R^p$ is H, 4"-$R^p$ is acetyl, m is 2, A is NH, B is —C(O)—$(CH_2)_q$—, q is 0, D is 1,3-phenylene, E is —$(CH_2)_r$—CH=CH—, r is 0, n is 1;

Compound of Formula (I), 2'-$R^p$ is H, 4"-$R^p$ is H, m is 2, A is NH, B is —C(O)—$(CH_2)_q$—, q is 0, D is 1,3-phenylene, E is —$(CH_2)_r$—CH=CH—, r is 0, n is 1;

Compound of Formula (I), 2'-$R^p$ is H, 4"-$R^p$ is acetyl, m is 2, A is NH, B is —C(O)—$(CH_2)_q$—, q is 0, D is 1,2-phenylene, E is —$(CH_2)_r$—CH=CH—, r is 0, n is 1;

Compound of Formula (I), 2'-R$^P$ is H, 4"-R$^P$ is H, m is 2, A is NH, B is —C(O)—(CH$_2$)$_q$—, q is 0, D is 1,2-phenylene, E is —(CH$_2$)$_r$—CH═CH—, r is 0, n is 1;

Compound of Formula (I), 2'-R$^P$ is H, 4"-R$^P$ is acetyl, m is 2, A is NH, B is —C(O)—(CH$_2$)$_q$—, q is 1, D is 1,2-phenylene, E is —(CH$_2$)$_r$—CH═CH—, r is 0, n is 1;

Compound of Formula (I), 2'-R$^P$ is H, 4"-R$^P$ is H, m is 2, A is NH, B is —C(O)—(CH$_2$)$_q$—, q is 1, D is 1,2-phenylene, E is —(CH$_2$)$_r$—CH═CH—, r is 0, n is 1;

Compound of Formula (I), 2'-R$^P$ is H, 4"-R$^P$ is acetyl, m is 0, A is absent, B is —N═CH—, D is 1,2-phenylene, E is —(CH$_2$)$_r$—CH═CH—, r is 0, n is 1;

Compound of Formula (I), 2'-R$^P$ is H, 4"-R$^P$ is acetyl, m is 0, A is NH, B is —(CH$_2$)$_q$—, q is 1, D is 1,2-phenylene, E is —(CH$_2$)$_r$—CH═CH—, r is 0, n is 1;

Compound of Formula (I), 2'-R$^P$ is H, 4"-R$^P$ is acetyl, m is 0, A is NH, B is —(CH$_2$)$_q$—, q is 1, D is 1,3-phenylene, E is —(CH$_2$)$_r$—CH═CH—, r is 0, n is 1;

Compound of Formula (I), 2'-R$^P$ is H, 4"-R$^P$ is acetyl, m is 2, A is NH, B is —(CH$_2$)$_q$—, q is 1, D is 1,3-phenylene, E is —(CH$_2$)$_r$—CH═CH—, r is 0, n is 1;

Compound of Formula (I), 2'-R$^P$ is H, 4"-R$^P$ is H, m is 2, A is NH, B is —(CH$_2$)$_q$—, q is 1, D is 1,3-phenylene, E is —(CH$_2$)$_r$—CH═CH—, r is 0, n is 1;

Compound of Formula (II), R$^P$ is H, m is 2, A is —O—; B is —(CH$_2$)$_q$—, q is 1, D is 1,2-phenylene, E is —(CH$_2$)$_r$—CH═CH—, r is 0, n is 1;

Compound of Formula (I), R$^P$ is acetyl, m is 2, A is —O—, B is absent, D is 3,4-quinolene, E is —(CH$_2$)$_r$—CH═CH—, r is 0, n is 1;

Compound of Formula (I), R$^P$ is acetyl, m is 1, A is absent, B is absent, D is absent, E is —(CH$_2$)$_r$—CH═CH—, r is 0, n is 1;

Compound of Formula (I), R$^P$ is H, m is 3, A is absent, B is absent, D is absent, E is absent, n is 1;

Compound of Formula (II), R$^P$ is H, m is 1, A is absent, B is absent, D is absent, E is —(CH$_2$)$_r$—CH═CH—, r is 0, n is 1;

Compound of Formula (I), R$^P$ is H, m is 2, A is absent, B is absent, D is absen, E is —(CH$_2$)$_r$—CH═CH—, r is 0, n is 1;

Compound of Formula (II), R$^P$ is H, m is 2, A is absent, B is absent, D is absent, E is —(CH$_2$)$_r$—CH═CH—, r is 0, n is 1;

Compound of Formula (I), R$^P$ is H, m is 1, A is absent, B is —CHOH—(CH2)$_q$—, q is 1, D is absent, E is —(CH$_2$)$_r$—CH═CH—, r is 0, n is 1;

Compound of Formula (I), R$^P$ is acetyl, m is 1, A is absent, B is —C(O)—(CH2)$_q$—, q is 1, D is absent, E is —(CH$_2$)$_r$—CH═CH—, r is 0, n is 1;

Compound of Formula (II), R$^P$ is H, m is 2, A is —NH—, B is —C(O)—(CH2)$_q$—, q is 0, D is 1,2-phenylene, E is —(CH$_2$)$_r$—CH═CH—, r is 0, n is 1;

Compound of Formula (I), R$^P$ is H, m is 1, A is absent, B is —CH(OH)—(CH$_2$)$_q$—, q is 0, D is absent, E is absent, n is 3;

Compound of Formula (I), R$^P$ is H, m is 1, A is absent, B is —CH(OH)—CH(OH)—(CH$_2$)$_q$—, q is 0, D is absent, E is absent, n is 1; and Compound of Formula (I), 2'-R$^P$ is H, 4"-RP is H, m is 2, A is NH, B is —C(O)—(CH$_2$)$_q$—, q is 0, D is 1,2-phenylene, E is —(CH$_2$)$_r$—CH═CH—, r is 1, n is 1.

Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 1 demonstrate the antibacterial activity of the compounds of the invention.

TABLE 1

Antibacterial Activity (MIC's) of Selected Compounds

| Microorganism | Organism code | Ery. A |
|---|---|---|
| Staphylococcus aureus ATCC 6538P | AA | 0.2 |
| Staphylococcus aureus A5177 | BB | 3.1 |
| Staphylococcus aureus A-5278 | CC | >100 |
| Staphylococcus aureus CMX 642A | DD | 0.39 |
| Staphylococcus aureus NCTC10649M | EE | 0.39 |
| Staphylococcus aureus CMX 553 | FF | 0.39 |
| Staphylococcus aureus 1775 | GG | >100 |
| Staphylococcus epidermidis 3519 | HH | 0.39 |
| Enterococcus faecium ATCC 8Q43 | II | 0.05 |
| Streptococcus bovis A-5169 | JJ | 0.02 |
| Streptococcus agalactiae CMX 508 | KK | 0.05 |
| Streptococcus pyogenes EES61 | LL | 0.05 |
| Streptococcus pyogenes 930 | MM | >100 |
| Streptococcus pyogenes PIU 2548 | NN | 6.2 |
| Micrococcus luteus ATCC 9341 | OO | 0.05 |
| Micrococcus luteus ATCC 4698 | PP | 0.2 |
| Escherichia coli JUHL | QQ | >100 |
| Escherichia coli SS | RR | 0.78 |
| Escherichia coli DC-2 | SS | >100 |
| Candida albicans CCH 442 | TT | >100 |
| Mycobacterium smegmatis ATCC 114 | UU | 3.1 |
| Nocardia Asteroides ATCC9970 | VV | 0.1 |
| Haemophilis Influenzae DILL AMP R | WW | 4 |
| Streptococcus Pheumoniae ATCC6303 | XX | 0.06 |
| Streptococcus Pheumoniae GYR 1171 | YY | 0.06 |
| Streptococcus Pheumoniae 5979 | ZZ | >128 |
| Streptococcus Pheumoniae 5649 | ZZA | 16 |

| Organism code | Example 4 | Example 6 | Example 10 | Example 11 | Example 12 | Example 13 |
|---|---|---|---|---|---|---|
| AA | 1.56 | 0.78 | 6.2 | 3.1 | 0.78 | 1.56 |
| BB | 25 | 12.5 | 25 | 50 | 0.78 | 6.2 |
| CC | >100 | >100 | 100 | >100 | >100 | >100 |
| DD | 1.56 | 1.56 | 6.2 | 3.1 | 0.78 | 1.56 |
| EE | — | 1.56 | 6.2 | — | 0.78 | 1.56 |
| FF | 1.56 | 0.78 | 6.2 | 3.1 | 0.78 | 1.56 |
| GG | >100 | >100 | 100 | >100 | >100 | >100 |
| HH | 1.56 | 0.78 | 6.2 | 3.1 | 0.78 | 1.56 |
| II | 0.39 | 0.39 | 0.78 | 0.2 | 0.1 | 0.2 |
| JJ | 0.2 | 0.1 | 0.39 | 0.1 | 0.05 | 0.1 |
| KK | 0.2 | 0.1 | 0.39 | 0.1 | 0.1 | 0.39 |
| LL | 0.39 | 0.2 | 0.78 | 0.2 | 0.05 | 0.2 |
| MM | >100 | >100 | 25 | >100 | 50 | 25 |
| NN | 12.5 | 12.5 | 6.2 | 12.5 | 0.39 | 12.5 |
| OO | 0.2 | 0.1 | 0.39 | 0.2 | 0.2 | 0.2 |
| PP | 1.56 | 0.78 | 1.56 | 3.1 | 0.39 | 0.39 |

TABLE 1-continued

Antibacterial Activity (MIC's) of Selected Compounds

| | | | | | | |
|---|---|---|---|---|---|---|
| QQ | 100 | 100 | >100 | >100 | >100 | >100 |
| RR | 6.2 | 3.1 | 6.2 | 6.2 | 1.56 | 25 |
| SS | >100 | >100 | >100 | >100 | >100 | >100 |
| TT | >100 | >100 | >100 | >100 | >100 | >100 |
| UU | 3.1 | 0.39 | 0.39 | 0.2 | 0.78 | 0.2 |
| VV | 0.2 | 0.39 | 1.56 | 0.2 | 0.78 | 0.78 |
| WW | 16 | 8 | 64 | 32 | 16 | 16 |
| XX | 0.03 | 0.03 | 0.12 | 0.12 | 0.25 | 0.5 |
| YY | 0.03 | 0.03 | 0.25 | 0.25 | 0.125 | 0.5 |
| ZZ | >128 | >128 | 64 | >128 | 128 | 64 |
| ZZA | 16 | 16 | 8 | 32 | 1 | 4 |

| Organism code | Example 14 | Example 15 | Example 16 | Example 17 | Example 18 | Example 19 |
|---|---|---|---|---|---|---|
| AA | 0.2 | 0.39 | 0.39 | 0.1 | 0.78 | 0.39 |
| BB | 3.1 | 3.1 | 0.39 | 6.2 | 0.78 | 3.1 |
| CC | >100 | >100 | >100 | >100 | >100 | >100 |
| DD | 0.2 | 0.39 | 0.39 | 0.2 | 0.78 | 0.78 |
| EE | 0.39 | 0.78 | 0.39 | 0.2 | 0.78 | 0.78 |
| FF | 0.2 | 0.39 | 0.39 | 0.1 | 0.78 | 0.78 |
| GG | >100 | >100 | >100 | >100 | >100 | >100 |
| HH | 0.2 | 0.39 | 0.39 | 0.2 | 1.56 | 0.78 |
| II | 0.1 | 0.1 | 0.2 | 0.05 | 0.39 | 0.1 |
| JJ | 0.05 | 0.05 | 0.2 | 0.01 | 0.2 | 0.02 |
| KK | 0.05 | 0.05 | 0.2 | 0.01 | 0.2 | 0.05 |
| LL | 0.05 | 0.1 | 0.2 | 0.02 | 0.2 | 0.05 |
| MM | >100 | >100 | >100 | >100 | >100 | >100 |
| NN | 6.2 | 6.2 | 0.39 | 25 | 1.56 | 12.5 |
| OO | 0.05 | 0.05 | 0.2 | 0.02 | 0.39 | 0.05 |
| PP | 0.39 | 0.39 | 0.39 | 0.1 | 0.78 | 0.78 |
| QQ | 50 | >100 | >100 | >100 | >100 | 25 |
| RR | 0.78 | 3.1 | 0.78 | 0.78 | 1.56 | 0.78 |
| SS | >100 | >100 | >100 | >100 | >100 | >100 |
| TT | >100 | >100 | >100 | >100 | >100 | >100 |
| UU | 0.78 | 1.56 | 6.2 | 0.2 | 12.5 | 0.39 |
| VV | 0.05 | 0.1 | 0.39 | 0.02 | 0.78 | 0.05 |
| WW | 8 | 32 | 32 | 8 | 128 | 8 |
| XX | 0.03 | 0.03 | 0.25 | 0.015 | 1 | 0.03 |
| YY | 0.03 | 0.03 | 0.25 | 0.015 | 0.5 | 0.03 |
| ZZ | >128 | >128 | >128 | >128 | >128 | >128 |
| ZZA | 16 | 16 | 0.5 | 8 | 2 | 16 |

| Organism code | Example 20 | Example 21 | Example 22 | Example 24 |
|---|---|---|---|---|
| AA | 3.1 | 1.56 | 1.56 | 0.78 |
| BB | 12.5 | 1.56 | 12.5 | 25 |
| CC | >100 | >100 | >100 | >100 |
| DD | 3.1 | 3.1 | 1.56 | 1.56 |
| EE | 3.1 | 3.1 | 1.56 | 1.56 |
| FF | 3.1 | 3.1 | 1.56 | 0.78 |
| GG | >100 | >100 | >100 | >100 |
| HH | 3.1 | 1.56 | 1.56 | 1.56 |
| II | 0.2 | 0.2 | 0.2 | 0.2 |
| JJ | 0.2 | 0.1 | 0.05 | 0.1 |
| KK | 0.39 | 0.1 | 0.1 | 0.1 |
| LL | 0.2 | 0.1 | 0.1 | 0.1 |
| MM | 100 | >100 | >100 | >100 |
| NN | 25 | 0.78 | 12.5 | 12.5 |
| OO | 0.2 | 0.2 | 0.1 | 0.1 |
| PP | 0.78 | 0.39 | 0.39 | 1.56 |
| QQ | >100 | >100 | 100 | 100 |
| RR | 3.1 | 1.56 | 0.78 | 6.2 |
| SS | >100 | >100 | >100 | >100 |
| TT | >100 | >100 | >100 | >100 |
| UU | 0.39 | 6.2 | 0.78 | 0.39 |
| VV | 0.2 | 0.39 | 0.1 | 0.1 |
| WW | 8 | 64 | 4 | 16 |
| XX | 0.25 | 0.25 | 0.06 | 0.03 |
| YY | 0.25. | 0.25 | 0.06 | 0.03 |
| ZZ | 128 | >128 | >128 | 128 |
| ZZA | 1 | 2 | 16 | 16 |

*missing data is indicated by "—"

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

The process for preparing a compound having the formula (I) or (II) wherein m, n, RP, A, B, and D are as defined previously and E is absent or is —CH═CH— comprises
(a) treating a compound having the formula 10

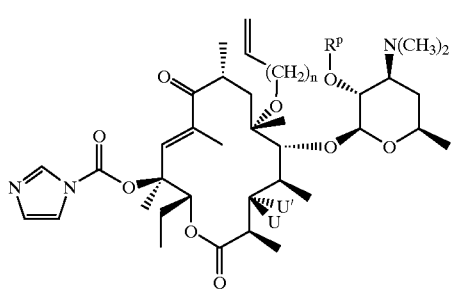

wherein U is 4"-RP-O-cladinose and U' is H, or U and U' taken together with the carbon atom to which they are attached form a carbonyl group, with a reagent compound having the formula $H_2N-(CH_2)_m-A-B-D-X^1$, wherein m, A, B, are as defined previously, D is as defined previously, and $X^1$ is a leaving group, to prepare an intermediate compound having the formula

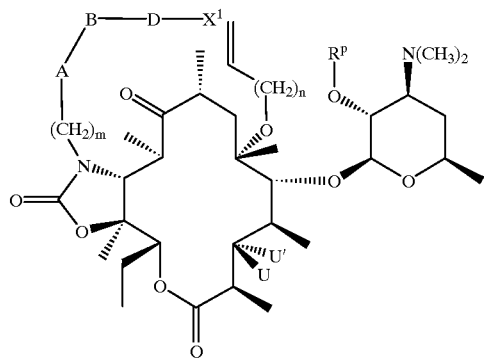

; and (b) cyclizing and optionally reducing the compound from Step (a).

In a preferred method of the process described above, m, n, RP, A, B, and D are as defined previously and E is absent or is —CH═CH—, U is 4"-RP-O-cladinose, and the product is a compound of formula (I).

In another preferred method of the process described above, m, n, RP, A, B, and D are as defined previously and E is absent or is —CH═CH—, U and U' are taken together with the carbon atom to which they are attached form a carbonyl group, and the product is a compound of formula (II). In a more preferred version of this process, the reagent of Step (a) is 2-((2-iodophenyl)methoxy)ethylamine.

Another method for preparing a compound having the formula (I) or (II) wherein m, n, RP, A, B, and D are as defined previously and E is absent or is —CH═CH—, is the method comprising
(a) treating a compound of formula 10, wherein U is 4"-RP-O-cladinose and U' is H, or U and U' taken together with the carbon atom to which they are attached form a carbonyl group, with a first reagent compound having the formula $H_2N-(CH_2)_m-A-X^2$, wherein m and A are as defined previously and $X^2$ is H, to prepare an intermediate compound having the formula

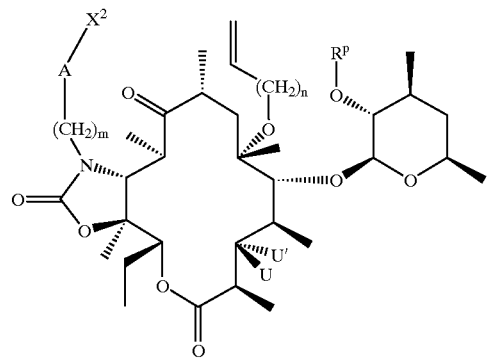

(b) treating the intermediate compound from Step (a) with a reagent compound having the formula $B'-D-X^1$, wherein $X^1$ is a leaving group, B' is a B-precursor moiety, and D is as defined previously, to prepare a second intermediate compound having the formula

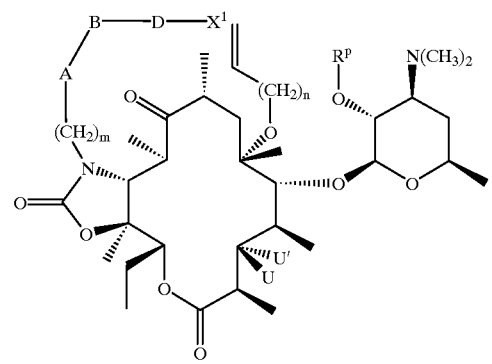

; and (b) cyclizing and optionally reducing the compound from Step (b).

In a preferred example of the method described immediately above, U is 4"-RP-O-cladinose, and the product is a compound of formula (I). In a more preferred method of this process the reagent of Step (a) having the formula $H_2N-(CH_2)_m-A-X^2$ is selected from the group consisting of hydrazine and ethylenediamine.

Still another for preparing a compound having the formula (I) or (II) wherein m, n, RP, A, B, and D are as defined previously and E is absent or is —CH═CH—, is the method comprising
(a) treating a compound of formula 10, wherein U is 4"-$R^P$-O-cladinose and U' is H, or U and U' taken together with the carbon atom to which they are attached form a carbonyl group, with a first reagent compound having the formula $H_2N-(CH_2)_m-A-X^2$, wherein m and A are as defined previously and $X^2$ is a N-protecting group, to prepare an intermediate compound having the formula

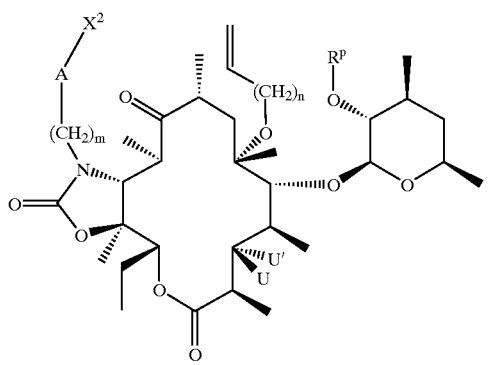

(b) treating the intermediate compound from Step (a) with a reagent compound having the formula B'—D—X¹, wherein X¹ is a leaving group B' is a B-precursor moiety, and D is as defined previously, to prepare an second intermediate compound having the formula

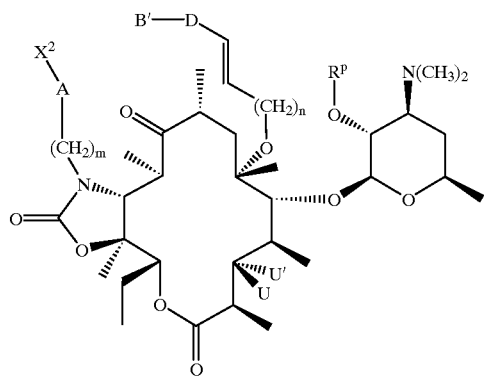

; and (b) cyclizing and optionally reducing the compound from Step (b).

In a preferred method of the process described immediately above, U is 4"—$R^P$-O-cladinose, and the product is a compound of formula (I).

Yet another example of the process of the invention comprises preparing a compound selected from the from the group consisting of formula (I) and (II), wherein A, B and D are as defined above, and E is restricted to the previously defined options (2)–(8) thereof, comprising (a) treating a compound having the formula

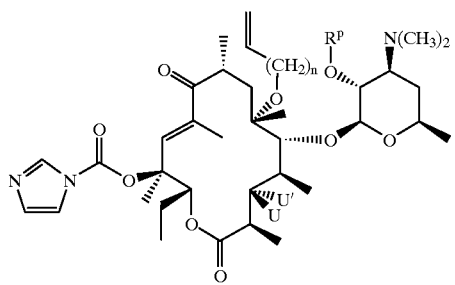

wherein U is 4"-$R^P$-O-cladinose, $R^P$ is a hydroxy protecting group, and U' is H, or U and U' taken together with the carbon atom to which they are attached form a carbonyl group, with a first reagent compound having the formula $H_2N$—$(CH_2)_m$—A—B—D—$X^3$, wherein m, A, B, D are as defined previously, to prepare a first intermediate compound having the formula

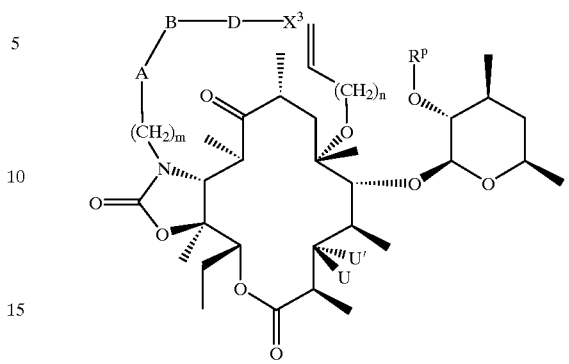

(b) treating the first intermediate compound from Step (a) with double bond modifying reagents, to prepare an second intermediate compound having the formula

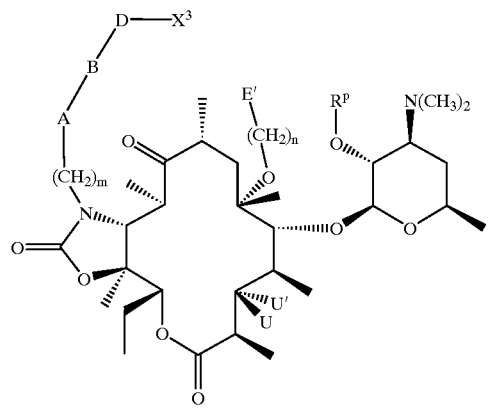

wherein E' is an E-precursor; and (c) cyclizing the compound from Step (b).

In a preferred method of this last process, U is 4"-$R^P$-O-cladinose, and the product is a compound of formula (I).

Abbreviations

Abbreviations which have been used in the descriptions of the scheme and the examples that follow are: DMF for dimethylformamide; DMSO for dimethylsulfoxide; EtOH for ethanol; HOAc for acetic acid; MeOH for methanol; $NaN(TMS)_2$ for sodium bis(trimethylsilyl)amide; and THF for tetrahydrofuran.

Synthetic Methods

The compounds and processes of the present invention will be better understood in connection with the Schemes 1–5 which illustrate the methods by which the compounds of the invention may be prepared. The compounds of the present invention are prepared by the representative methods described below. The groups A, B, D, E, m, n and $R^P$ are as defined previously. Schemes 1–5 are shown following the text section below.

The preparation of the compounds of the invention of formula (I)–(V) from erythromycin A is outlined in Schemes 1–5. The preparation of protected erythromycin A is described in the following United States patents, U.S. Pat. No. 4,990,602; U.S. Pat. No. 4,331,803, U.S. Pat. No. 4,680,368, and U.S. Pat. No. 4,670,549 which are incorporated by reference. Also incorporated by reference is European Patent Application EP 260,938.

As shown in Scheme 1, the C-9-carbonyl group of compound 1 is protected with an oxime to give the compound 2, wherein V is =N—O—$R^a$ or =N—O—C($R^b$)($R^c$)—O—$R^a$ where $R^a$ is defined above and $R^b$ and $R^c$ are each independently selected from the group consisting of (a) hydrogen, (b) unsubstituted $C_1$–$C_{12}$-alkyl, (c) $C_1$–$C_{12}$-alkyl substituted with aryl, and (d) $C_1$–$C_{12}$-alkyl substituted with substituted aryl, or $R^b$ and $R^c$ taken together with the carbon to which they are attached form a $C_3$–$C_{12}$-cycloalkyl ring. An especially preferred carbonyl protecting group V is O-(1-isopropoxycyclohexyl) oxime.

The 2'- and 4"-hydroxy groups of 2 are protected by reaction with a suitable hydroxy protecting reagent, such as those described by T. W. Greene and P. G. M. Wuts in *Protective Groups in Organic Synthesis,* 2nd ed., John Wiley & Son, Inc., 1991, which is incorporated by reference. Hydroxy protecting groups include, for example, acetic anhydride, benzoic anhydride, benzyl chloroformate, hexamethyldisilazane, or a trialkylsilyl chloride in an aprotic solvent. Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof. Protection of 2'- and 4"-hydroxy groups of 2 may be accomplished sequentially or simultaneously to provide compound 3 where $R^p$ is a hydroxy protecting group. Preferred RP protecting groups include acetyl, benzoyl and trimethylsilyl.

The 6-hydroxy group of compound 3 is then alkylated by reaction with an alkylating agent in the presence of base to give compound 4. Alkylating agents include alkyl chlorides, bromides, iodides or alkyl sulfonates. Specific examples of alkylating agents include allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromochloromethane, bromomethyl phenyl sulfone, 1,3-dibromo-1-propene, and the like. Examples of alkyl sulfonates are: allyl O-tosylate, 3-phenylpropyl-O-trifluoromethane sulfonate, n-butyl-O-methanesulfonate and the like. Examples of the solvents used are aprotic solvents such as dimethylsulfoxide, diethylsulfoxide, N,N-dimethylformamide, N,N-dimethylacetamide, N-methyl-2-pyrrolidone, hexamethylphosphoric triamide, a mixture thereof or a mixture of one of these solvents with ether, tetrahydrofuran, 1,2-dimethoxyethane, acetonitrile, ethyl acetate, acetone and the like. Examples of the base which can be used include potassium hydroxide, cesium hydroxide, tetraalkylammonium hydroxide, sodium hydride, potassium hydride, potassium isopropoxide, potassium tert-butoxide, potassium isobutoxide and the like.

The preferred intermediate compound 4 of this invention is one wherein R is allyl.

The deprotection of the 2'- and 4"-hydroxyl groups is then carried out according to methods described in literature, for example, by T. W. Greene and P. G. M. Wuts in *Protective Groups in Organic Synthesis,* 2nd ed., John Wiley & Son, Inc., 1991, which is incorporated herein by reference. The conditions used for the deprotection of the 2'- and 4"-hydroxyl groups usually results in the conversion of X to =N—OH. (For example, using acetic acid in acetonitrile and water results in the deprotection of the 2'- and 4"-hydroxyl groups and the conversion of X from =N—O—$R^a$ or =N—O—C($R^b$)($R^c$)—O—$R^a$ where $R^a$, $R^b$ and $R^c$ are as defined above to =N—OH). If this is not the case, the conversion is carried out in a separate step.

The deoximation reaction can be carried out according to the methods described in the literature, for example by Greene (op. cit.) and others. Examples of the deoximating agent are inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate, potassium metabisulfite and the like. Examples of the solvents used are protic solvents such as water, methanol, ethanol, propanol, isopropanol, trimethylsilanol or a mixture of one or more of the mentioned solvents and the like. The deoximation reaction is more conveniently carried out in the presence of an organic acid such as formic acid, acetic acid and trifluoroacetic acid. The amount of acid used is from about 1 to about 10 equivalents of the amount of compound 5 used. In a preferred embodiment, the deoximation is carried out using an organic acid such as formic acid in ethanol and water to give the desired 6-O-substituted erythromycin compound 6. In the preferred process of this invention, R is allyl in compound 6.

Scheme 2 illustrates the methods used to prepare intermediate compounds of the invention. The 6-O-substituted compound 6 may be converted to a hydroxy-protected compound 7 by procedures referenced previously.

Compound 7 is treated by mild aqueous acid hydrolysis or by enzymatic hydrolysis to remove the cladinose moiety and give compound 8. Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol and the like. Reaction times are typically 0.5 to 24 hours. The reaction temperature is preferably –10 to 35° C.

Compound 8 may be converted to compound 9 by oxidation of the 3-hydroxy group to an oxo group using a Corey-Kim reaction with N-chlorosuccinimide-dimethyl sulfide, or with a modified Swern oxidation procedure using carbodiimide-dimethylsulfoxide. In a preferred reaction, 8 is added into a pre-formed N-chlorosuccinimide and dimethyl sulfide complex in a chlorinated solvent such as methylene chloride at –10 to 25° C. After stirring for about 0.5 to about 4 hours, a tertiary amine such as triethylamine or Hunig's base is added to produce the ketone 9.

Compounds 7 and 9 can then treated with an excess of sodium hexamethyldisilazide or a hydride base in the presence of carbonyldiimidazole in an aprotic solvent for about 8 to about 24 hours at about –30° C. to room temperature to give compounds 10a and 10b, respectively. The hydride base may be, for example, sodium hydride, potassium hydride, or lithium hydride, and the aprotic solvent may be one as defined previously. The reaction may require cooling or heating from about –20° C. to about 70° C., depending on the conditions used, and preferably from about 0° C. to about room temperature. The reaction requires about 0.5 hours to about 10 days, and preferably about 10 hours to 2 days, to complete. Portions of this reaction sequence follow the procedure described by Baker et al., *J. Org. Chem.,* 1988, 53, 2340, which is incorporated herein by reference.

Scheme 3 illustrates several routes for the preparation of compounds of formulas (I) and (II). One skilled in the art will be able to easily decide which approach is to be utilized, depending upon the product that is desired.

In one preferred route, when a $H_2N$—$(CH_2)_m$—A—B—D-precursor can be prepared conveniently, compounds 10a and 10b can be reacted with the precursor in the presence of a suitable base to give compounds 12a and 12b, respectively. A suitable $H_2N$—$(CH_2)_m$—A—B—D-precursor compound is one such as $H_2N$—$(CH_2)_m$—A—B—D—$X^1$, wherein A, B, D and m are as defined previously and $X^1$ is a suitable leaving group. Suitable bases include, for example, triethylamine and Hunig's base, and suitable leaving groups include, but are not limited to Cl, Br, I and trifluoromethanesulfonate. When D is selected from options (6)–(15) as defined previously, the D moiety precursor or precursors may be available commercially or prepared by standard methods known to those skilled in the art.

To prepare compounds (I) and (II) wherein m is 0 and A is —O—, the $H_2N$—$(CH_2)_m$—A—B—D—$X^1$ reagent is a hydroxylamine compound $H_2N$—O—B—D—$X^1$, wherein m is 0 and B, D and $X^1$ are as described previously. These compounds may be prepared by a two-step reaction which involves reacting N-hydroxyphthalimide with an appropriate alcohol and cleaving the intermediate with hydrazine, as described by Grochowski and Jurczak, *Synthesis,* 682–683, (1976), for example. The preparation of the intermediates and precursors to the desired hydroxylamine reagent from standard starting materials and reactions will be easily accomplished by those skilled in the art.

To prepare compounds (I) and (II) wherein m is not 0 and A is —O—, the $H_2N$—$(CH_2)_m$—A—B—D—$X^1$ reagent is an amino ether compound having the formula $H_2N$—$(CH_2)_m$—O—B—D—$X^1$, wherein m is not 0 but is otherwise as previously defined, and B, D and X are as defined previously. These compounds may be prepared from a suitable amino alcohol by a two-step reaction (cf. Grochowski and Jurczak, op. cit.) which involves first converting the amino group of an amino alcohol compound into a phthalimide derivative. The free hydroxyl group of the derivatized molecule is then reacted with an appropriate reagent to form the desired B moiety, and the phthalimide protecting group is removed by treatment with hydrazine to give the desired amino ether compound. For example, $H_2N$—$(CH_2)_m$—A—B—D—$X^1$ reagents having the formulas $H_2N$—$(CH_2)_m$—O—$(CH_2)_q$—D—$X^1$, $H_2N$—$(CH_2)_m$—O—C(O)—$(CH_2)_q$—D—$X^1$, $H_2N$—$(CH_2)_m$—O—C(O)—O—$(CH_2)_q$—D—$X^1$, $H_2N$—$(CH_2)$—O—C(O)—$NR^1$—$(CH_2)_q$—D—$X^1$ and $H_2N$—$(CH_2)_m$—O—C(O)—$NR^1$—$(CH_2)_q$—D—$X^1$ may be prepared in this manner. The preparation of the desired compound may be accomplished without undue effort by those skilled in the art.

Also shown in Scheme 3 is an alternate route for the preparation of intermediate compounds 12a and 12b. This multi-step approach is preferred when a $H_2N$—$(CH_2)_m$—A—B—D-precursor compound cannot be conveniently prepared in advance. This may occur, for example, in the case wherein A is —O— or —$N(R^1)$— and B is desired to be —C(O)—$(CH_2)_q$—, —C(O)—O—$(CH_2)_q$—, or —C(O)—$NR^1$—$(CH_2)_q$—.

In one example of this alternate route, compounds 10a and 10b are treated with a reagent compound having the formula $H_2N$—$(CH_2)_m$—A—$X^2$, wherein m and A are as defined previously and $X^2$ is H or when A is —NH—, may also be a N-protecting group, to give the intermediate compounds 11a and 11b. For example, when m is 0 and A is —$N(R^1)$—, wherein $R^1$ is H, this reagent is hydrazine and produces intermediates 11a and 11b, wherein m is 0, A is —NH— and $X^2$ is H.

The intermediates 11a and 11b, wherein m is 0, A is —NH— and $X^2$ is H may then be reacted with a reagent having the formula B'—D—$X^1$, wherein B' is a precursor of the B-moiety. For example, when B'—D—$X^1$ is an aldehyde having the formula H—C(O)—$(CH_2)_q$—D—$X^1$, B' is H—C(O)— and q and D are as defined previously, and the reaction produces compounds 12a and 12b wherein m is 0, A is absent and B is —N=CH— and q and D are as defined previously. Reduction of the imine function of these intermediate compounds with a borohydride reducing agent provides compounds 12a and 12b wherein m is 0, A is —NH—, B is —NH—$(CH_2)_q$—, q is at least 1 and D is as defined previously.

In another example of this route, when compounds 10a and 10b are treated with a diamine reagent compound having the formula $H_2N$—$(CH_2)_m$—A—$X^2$, wherein m is not 0, A is —$N(R^1)$— and $X^2$ is H or a N-protecting group, the intermediates 11a and 11b wherein m is not 0, A is —$N(R^1)$— and $X^2$ is H or a N-protecting group are prepared. If N-protected, these intermediates may be deprotected by standard reactions to give compounds wherein $X^2$ is H.

These compounds 11a and 11b wherein $X^2$ is H may then be reacted with reagents of the formula B'—D—$X^1$, wherein B' is a precursor of the B-moiety and $X^1$ is as defined previously, to give the compounds 12a and 12b wherein A is —$N(R^1)$— and B is —C(O)—$(CH_2)_q$—. Examples of such B'—D—$X^1$ reagents include acylating reagents, for example, acid halides having the formula halogen-C(O)—$(CH_2)_q$—D—$X^1$. Other acylating agents may be acid anhydrides of the formula O(C(O)—D—$X^1$)$_2$, or free acids of the formula HO—C(O)—$(CH_2)_q$—D—$X^1$ in the presence of an activation agent such as a carbodiimide. One suitable carbodiimide reagent is 1-(3-dimethylaminopropyl)-3-ethylcarbodiimide hydrochloride.

Other B'—D—$X^1$ reagents include carbonating reagents of the type halogen-C(O)—O—$(CH_2)_q$—D—$X^1$ or O(C(O)—O—$(CH_2)_q$—D—$X^1$)$_2$, which give the compounds 12a and 12b wherein A is —NH— and B is —C(O)—O—$(CH_2)_q$—. Still other B'—D—$X^1$ reagents include carbamating reagents of the type halogen-C(O)—$N(R^1)$—$(CH_2)_q$—D—$X^1$, which result in the compounds 12a and 12b wherein A is —$N(R^1)$— and B is —C(O)—$N(R^1)$—$(CH_2)_q$—.

The intermediates 11a and 11b, wherein m is 0, A is —NH— and $X^2$ is H, prepared as described earlier, may also be reacted with appropriate B'—D—$X^1$ acylating agents, carbonating agents or carbamylating agents to give desired intermediate compounds 12a and 12b wherein m is 0, A is —NH— and B is —C(O)—$(CH_2)_q$—, —C(O)—O—$(CH_2)_q$—, or —C(O)—$NR^1$—$(CH_2)_q$—.

In yet another example of this multi-step route, compounds 10a and 10b are treated with an amino alcohol $H_2N$—$(CH_2)_m$—OH, wherein m is 2–7, to give intermediates 11a and 11b wherein m is 2–7, A is —O— and $X^2$ is H. The newly introduced free hydroxyl group of these intermediates may then be subjected to various reactions in order to prepare additional intermediates. For example, the free hydroxyl group may be reacted with acylating reagents, carbonating reagents or carbamating reagents as described previously to provide compounds wherein A is —O— and B is —C(O)—(CH$_2$)$_q$—, —C(O)—O—(CH$_2$)$_q$— or —C(O)—N(R1)—(CH$_2$)$_q$—, respectively. The hydroxyl group may also be converted by use of standard reactions to a sulfonate, which is then converted to an azide, which can in turn be reduced to give an amino compound. These newly formed 11a and 11b compounds wherein A is now —NH— and X$^2$ is H may be treated with appropriate B'—D—X$^1$ acylating reagents, carbonating reagents or carbamating reagents as described previously to provide compounds wherein B is —C(O)—(CH$_2$)$_q$—, —C(O)—O—(CH$_2$)$_q$— or —C(O)—N(R1)—(CH$_2$)$_q$—, respectively.

Once compounds 12a and 12b have been prepared it is possible to close the ring and prepare compounds 14a and 14b. In the instances wherein D is present and E is —CH═CH—, this is generally accomplished by means of a Heck reaction in the presence of (Pd(II) or Pd(O), phosphine, and amine or inorganic base (see *Organic Reactions,* 1982, 27, 345–390). When D is alkenylene, an olefin metathesis reaction may be utilized to close the ring (cf. R. H. Grubbs, S. J. Miller, and G. G. Fu, *Acc. Chem. Res.,* 28, 446, (1995)). The alkenylene may then be oxidized to a glycol (—CH(OH)—CH(OH)—) with reagents such as osmium tetroxide and morpholine N-oxide.

Also shown in Scheme 3 is yet another route for the preparation of compounds of formula (I) and (II). According to this procedure, compounds 11a and 11b are treated with a B'—D—X$^1$ reagent, wherein D is present and B' is as previously defined, by means of a Heck reaction as described above to give compounds 13a and 13b. At this point, ring closure is achieved by a reaction at the X$^2$ and B' moieties of 13a and 13b. When A is O and X$^2$ is H, then ring closure to give compounds 14a and 14b wherein B is —C(O)—(CH$_2$)$_q$—, —C(O)—O—(CH$_2$)$_q$—, or —C(O)—NR$^1$—(CH$_2$)$_q$—, may be accomplished most easily when B' is part of selected acylating reagents, carbonating reagents or carbamating reagents as described previously. The carbonyl group of —C(O)—(CH$_2$)$_q$— can be reduced to —C(OH)—(CH$_2$)$_q$— with reducing agents such as NaBH$_4$, NaBH$_3$CN, and the like.

Optional deprotection of compounds 14a and 14b as described previously gives 15a and 15b which are compounds of formula (I) and (II) of the invention, respectively, wherein E is —CH═CH—.

It is possible to reduce the double bond of compounds 15a and 15b to give the corresponding —CH$_2$—CH$_2$— compounds, which are structures of formula (I) and (II) wherein E is absent and n is at least 2, when such compounds are desired. Scheme 4 illustrates the preparation of additional compounds of the invention wherein E is other than —CH═CH—. In order to prepare these compounds, it is necessary to modify a double bond of an intermediate compound of the invention. This is most easily accomplished by first reacting compound 10a or 10b with a new reagent H$_2$N—(CH$_2$)$_m$—A—B—D—X$^3$, wherein m is as defined previously and X$^3$ is —(CH$_2$)$_r$—Y, wherein r is 0, 1, 2, 3 or 4 and Y may be a N-precursor, an acyl-precursor, hydroxyl or —CH$_2$—I moiety, to prepare the new intermediate compounds 16a and 16b.

An acyl precursor may be a moiety such as C(O)—X*, wherein X* is H or a leaving group, or the acyl precursor may be an acyloxy group.

Suitable N-precursor moieties are N-protected amino groups, such as acylamino groups which can be deprotected to a free amino group, or groups such as —N$_3$ and —NO$_2$, which can be reduced to amino groups.

After the Heck reaction has been performed, it is possible to reduce the —CH═CH— double bond by the use of hydrogen in the presence of a Pd/C catalyst. This reduction allows for the preparation of compounds of the invention wherein E is arylene-CH$_2$—CH$_2$— or arylene-CH$_2$—CH$_2$—.

Shown in the bottom half of Scheme 4 are additional reactions which may be performed with a double bond modifying reagent when E is —CH═CH—. The moiety M' is a shorthand representation of the macrolide moiety to which the 6—O—(CH$_2$)$_n$—CH═CH$_2$— moiety is attached. Examples of the double bond modifying reagents follow below. For example, compounds 16a and 16b can be treated with perchloric acid to convert the —CH═CH— moiety into an epoxy moiety to give compounds 17a and 17b, respectively. Compounds 16a and 16b can be treated with ozone, or OsO$_4$ and NaIO$_4$ to give the aldehyde compounds 18a and 18b, respectively. The aldehyde compounds 18a and 18b can then be reduced to the alcohol compounds 19a and 19b, respectively, by treatment with a borohydride reducing agent, such as sodium borohydride or potassium borohydride. Alternately, compounds 18a and 18b can be converted to the amine compounds 20a and 20b, respectively, by reductive amination with an amine of formula R$^1$NH$_2$ in the presence of a reducing agent such as NaBH$_3$CN or H$_2$ and Pd/C. Or, the aldehyde compounds 18a and 18b can be converted to the carboxy compounds 21a and 21b, respectively, by oxidation with Jones reagent.

Scheme 5 illustrates further the conversion of compounds 18a, 18b, 19a, 19b, 20a, 20b, 21a, or 21b, prepared in Scheme 4, to compounds (I) or (II) of the invention. The variable E' represents a E-precursor moiety, such as the groups described in Scheme 4, for example —CH(O), —OH, —NH$_2$, —C(O)OH, or an epoxy ring of the compounds.

In compounds 16a and 16b, X$^3$ is —(CH$_2$)$_r$—Y, wherein r and Y are as defined above.

Suitable N-precursor moieties are N-protected amino groups, such as acylamino groups which can be deprotected to a free amino group, or groups such as —N$_3$ and —NO$_2$, which can be reduced to amino groups. The amino group can then be used as a reagent to react with the newly formed epoxy group of compounds 17a and 17b to form compounds of formula (I) or (II) wherein E is —(CH$_2$)$_r$—NR$^1$—CH$_2$—CH(OH)—. The amino group can also be used as a reagent to react with the newly formed aldehyde group of compounds 18a and 18b to form imine compounds which are subsequently reduced with hydrogen in the presence of a Pd or Pt catalyst to give compounds of formula (I) or (II) wherein E is —(CH$_2$)$_r$—N(R$^1$)—. The amino group can also be used as a reagent to react with the newly formed carboxyl group of compounds 21a and 21b to form compounds of formula (I) or (II) wherein E is (CH$_2$)$_r$—N(R$^1$)—C(O)—. In some instances it may be possible to react the N-protected acylamino moieties with the desired newly formed function groups to give the desired compounds of formula (I) or (II).

Scheme 1
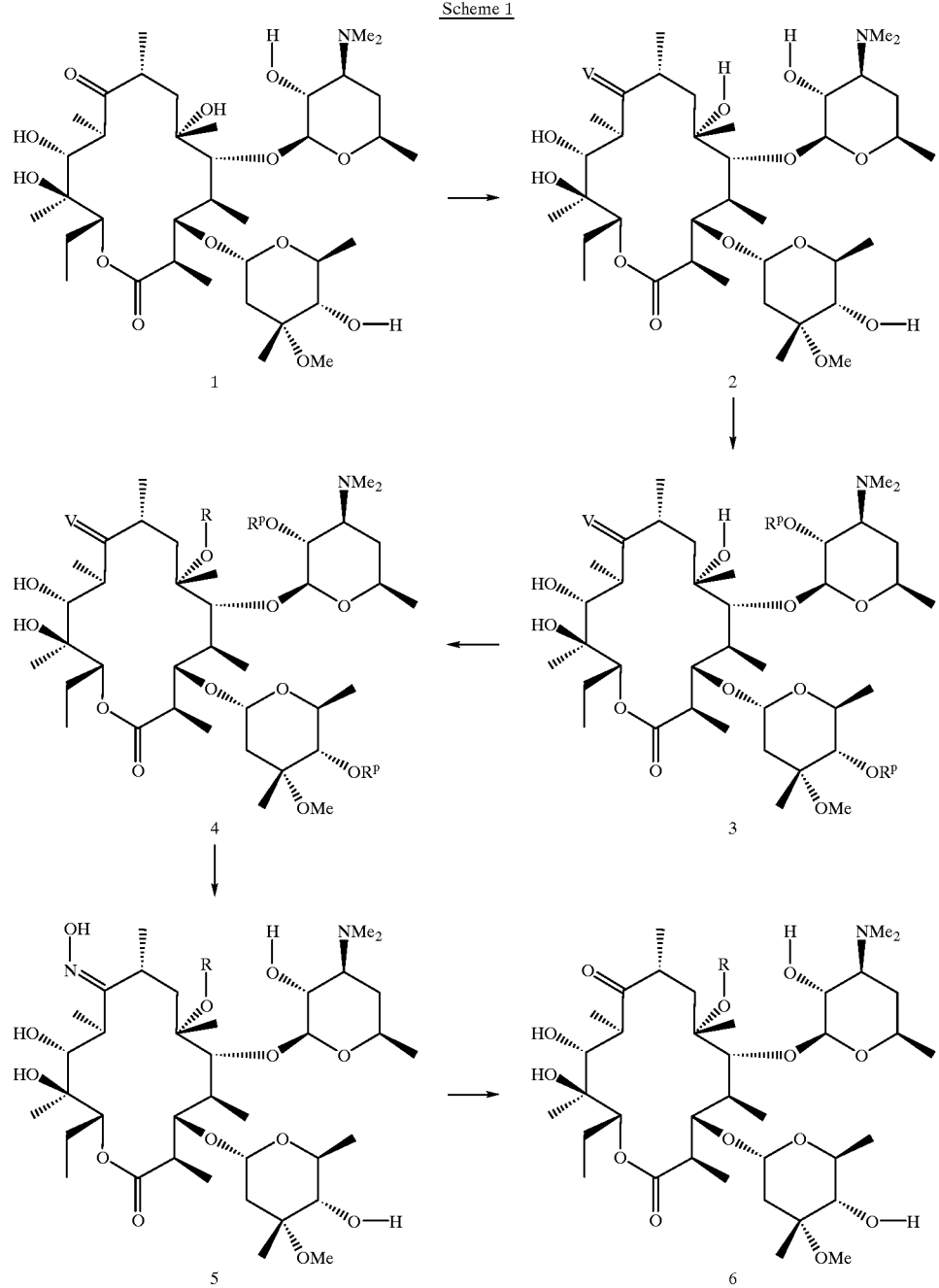

Scheme 2
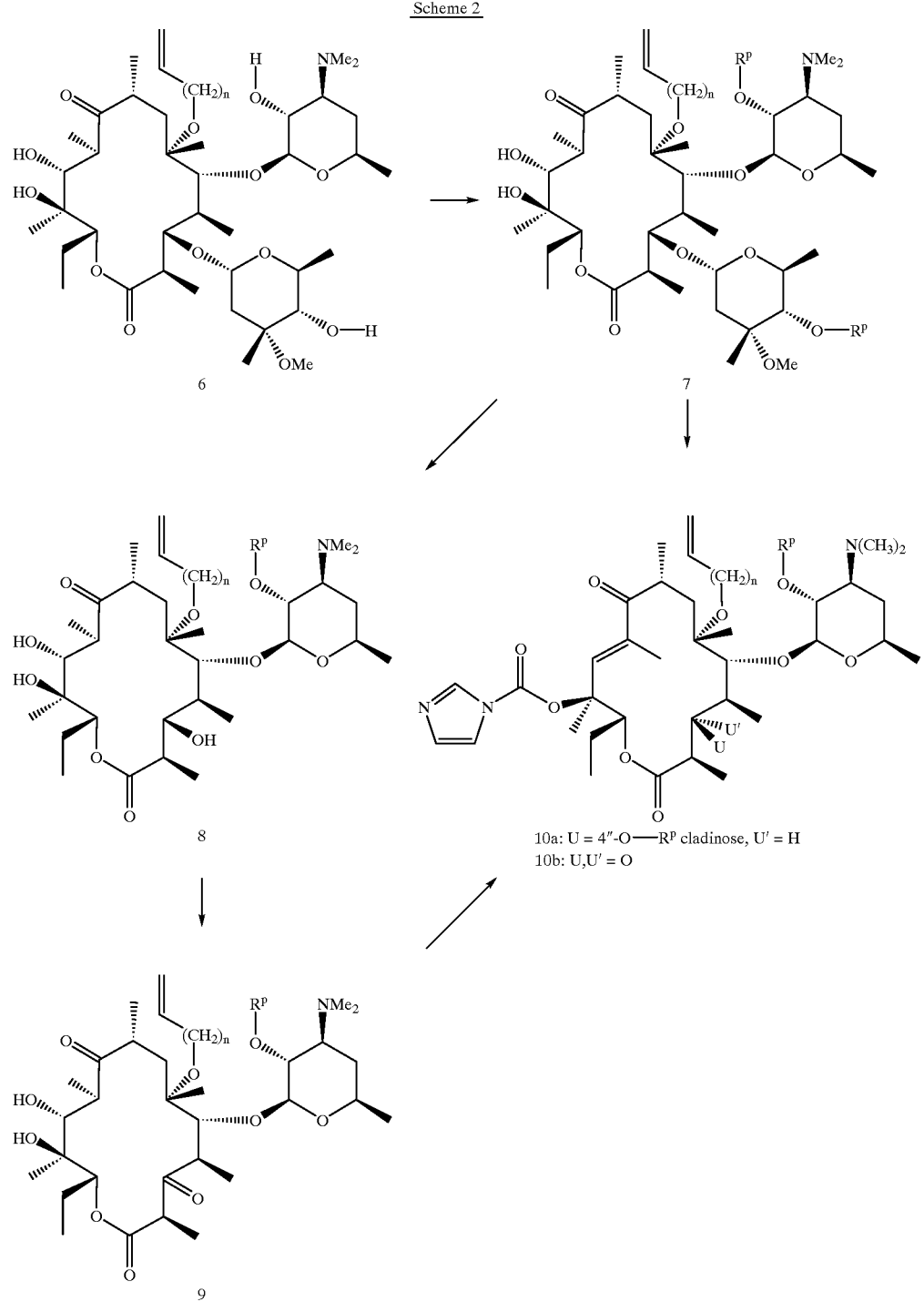

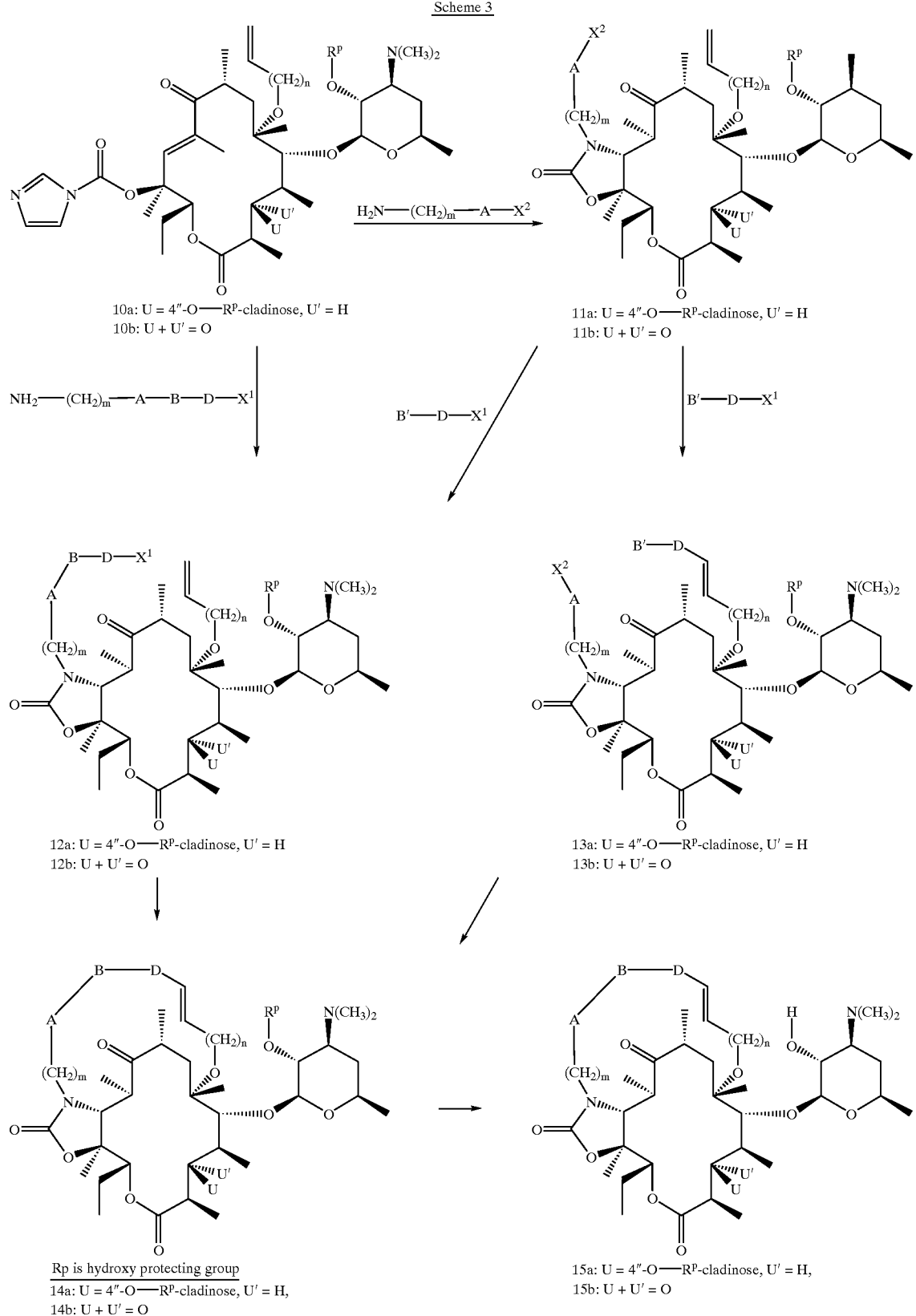

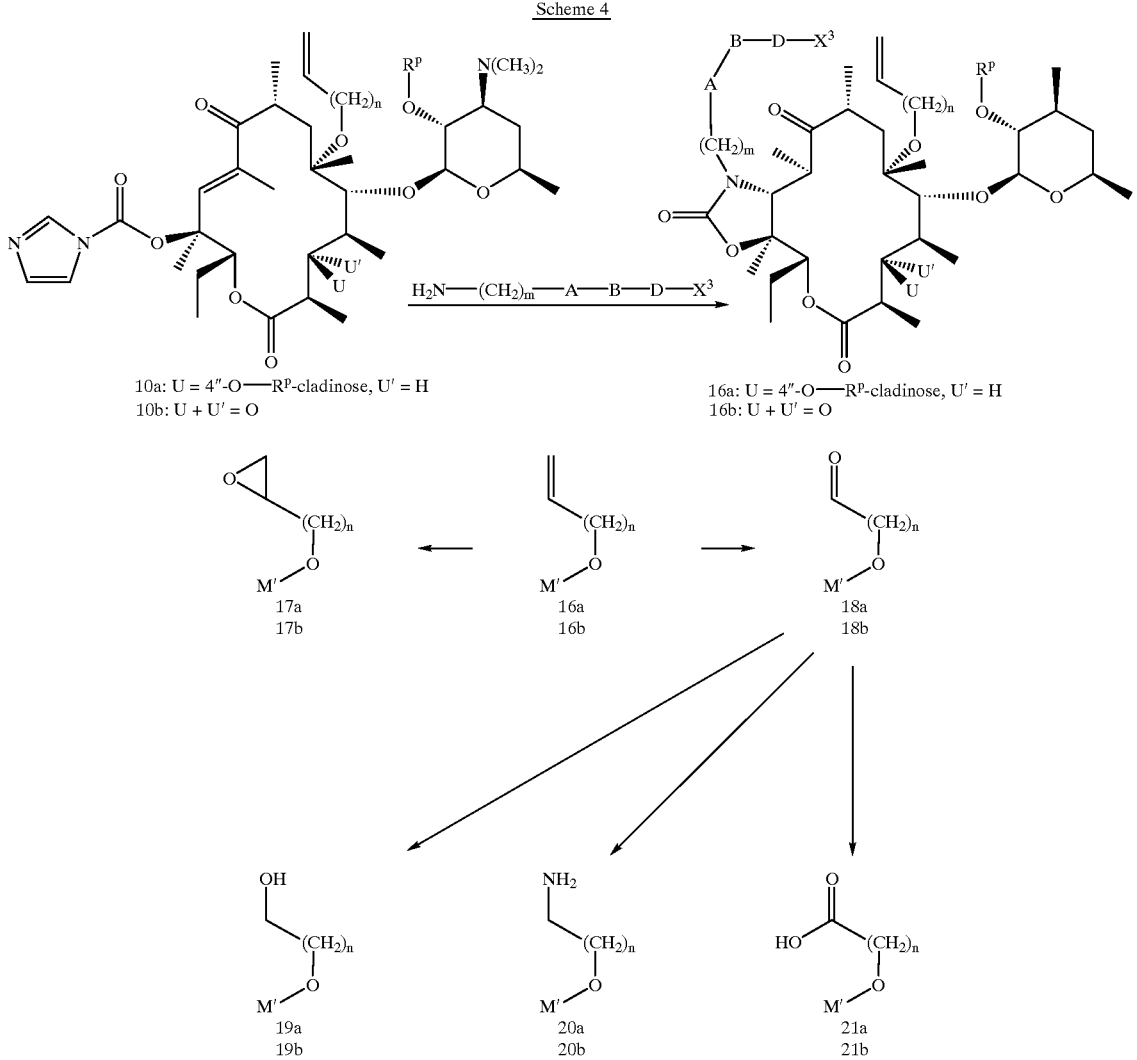

An acyl precursor may be a moiety such as C(O)—X*, wherein X* is H or a leaving group, or the acyl precursor may be an acyloxy group. These precursors may react with the hydroxyl group of newly formed compounds 19a and 19b to form compounds of formula (I) or (II) wherein E is —(CH$_2$)$_r$—C(O)—O—, or they may react with the newly formed compounds 20a and 20b to form compounds of formula (I) or (II) wherein E is —(CH$_2$)$_r$—C(O)—N(R$^1$)—.

When Y of the X$^3$ group is a hydroxyl group it may be reacted with the carboxyl croup of newly formed compounds 21a and 21b to form compounds of formula (I) or (II) wherein E is —(CH$_2$)$_r$—O—C(O)—.

When Y of the X$^3$ group is a —CH$_2$—I group it may be reacted with the hydroxyl group of newly formed compounds 19a and 19b to form compounds of formula (I) or (II) wherein E is —(CH$_2$)$_r$—O—.

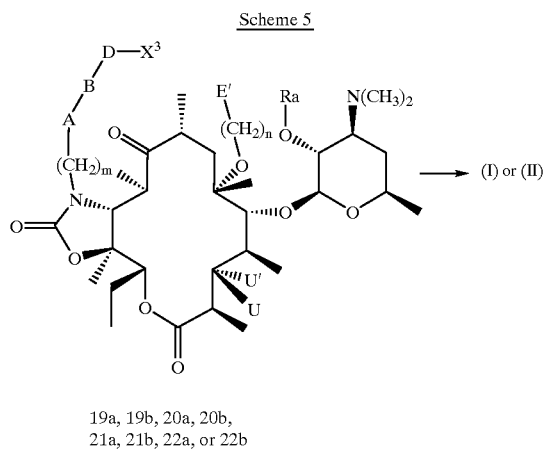

19a, 19b, 20a, 20b,
21a, 21b, 22a, or 22b

It will be appreciated by one skilled in the art that the decision as to when to perform certain of the reactions described above may be dependent upon the presence of reactive moieties within the molecule. Therefore, suitable protection and deprotection steps may be required from time to time, as are well known and applied within the art.

The foregoing may be better understood by reference to the following examples which are presented for illustration and not to limit the scope of the inventive concept.

EXAMPLE 1

Compound of Formula (I), 2'-$R^p$ is H, 4"-$R^p$ is acetyl, m is 2, A is NH, B is —C(O)—$(CH_2)_q$—, q is 0, D is 1,3-phenylene, E is —$(CH_2)_r$—CH=CH—, r is 0, n is 1

Step 1a: Compound 4 from Scheme 1: V is N—O—(1-isopropoxycyclohexyl), R is allyl, $R^p$ is trimethylsilyl To a 0° C. solution of 2',4"-bis-O-trimethylsilylerythromycin A 9-[O-(1-isopropoxycyclohexyl)oxime (1.032 g, 1.00 mmol, prepared according to the method of U.S. Pat. No. 4,990,602) in 5 mL of DMSO and 5 mL of THF was added freshly distilled allyl bromide (0.73 mL, 2.00 mmol). After approximately 5 minutes, a solution of potassium tert-butoxide (1M 2.0 mL, 2.0 mL) in 5 mL of DMSO and 5 mL of THF was added dropwise over 4 hours. The reaction mixture was taken up in ethyl acetate and washed with water and brine. The organic phase was concentrated in vacuo to give the desired compound (1.062 g) as a white foam.

Step 1b: Compound 5 from Scheme 1: V is NOH. R is allyl

To a solution of the compound from Step 1a (1.7 g) in 17 mL of acetonitrile and 8.5 mL of water was added 9 mL of acetic acid at ambient temperature. After several hours, the reaction mixture was diluted with 200 mL of toluene and concentrated in vacuo. The residue obtained was found to contain unreacted starting material, so additional acetonitrile (15 mL), water (70 mL) and acetic acid (2 mL) was added. After 2 hours, an additional 1 mL aliquot of acetic acid was added. After approximately three more hours, the reaction mixture was placed in the freezer overnight. The reaction mixture was allowed to warm to ambient temperature, diluted with 200 mL of toluene and concentrated in vacuo. The residue was chased twice with toluene and dried to constant weight (1.524 g).

Step 1c: Compound 6 from Scheme 1: R is allyl

The compound from Step 1b (1.225 g) in 16 mL of 1:1 ethanol-water was treated with $NaHSO_3$ (700 mg) and formic acid (141 μL) at 86° C. for 2.5 hours. The reaction mixture was allowed to cool to ambient temperature, diluted with 5–6 mL of water, basified with 1 N NaOH to pH 9–10 and extracted with ethyl acetate. The combined organic extracts were washed with brine, dried over $MgSO_4$, filtered and concentrated in vacuo. The crude material was purified by column chromatography, eluting with 1% MeOH in methylene chloride containing 1% ammonium hydroxide, to give 686 mg (57%) of the title compound. $^{13}C$ NMR ($CDCl_3$) δ219.3 (C-9), 174.8 (C-1), 135.5 (C-17), 116.3 (C-18), 101.9 (C-1'), 95.9 (C-1"), 79.7 (C-5), 78.8 (C-6), 78.5 (C-3), 74.1 (C-12), 72.4 (C-3"), 70.6 (C-11), 68.1 (C-5'), 65.5 (C-16), 65.1 (C2'), 49.0 (C-3" O—$CH_3$), 45.0 (C-2), 44.1 (C-8), 39.7 ($NMe_2$), 37.9 (C-4), 37.1 (C-10), 34.6 (C-2"), 28.4 (C-4'), 21.0, 20.6 (C-3"$CH_3$, C-6' $CH_3$), 20.8 (C-14), 18.3 (C-6"), 18.1 (C-8 $CH_3$), 15.7, 15.6 (C-2 $CH_3$, C-6 $CH_3$), 11.9 (C-10 $CH_3$), 10.1 (C-15), 8.9 (C-4 $CH_3$). MS (FAB)+n/e 774 $[M+H]^+$, 812 $[M+K]^+$.

Step 1d. Compound 7 of Scheme 2, $R^p$ is acetyl

To a solution of the compound from Example 1c (80 g, 103 mmol and DMAP (4.0 g, 32.7 mmol) in dichloromethane (200 mL) was added acetic anhydride (40 mL, 400 mmol). The solution was stirred for 5 hours at ambient temperature, and the mixture was diluted with dichloromethane (800 mL). The organic phase was washed with 5% $Na_2CO_3$, saturated $NaHCO_3$ and brine, and dried over $MgSO_4$. The solvent was removed under vacuum, and the residue was dried. The residue was crystallized from acetonitrile to give the title compound (60.0 g). MS (APCI) m/z 858 $[M+H]^+$.

Step 1e. Compound 10a of Scheme 3. $R^p$ is acetyl

To a solution of the compound from Step 1d (42.85 g, 50 mmol) in THF (250 mL) cooled to −40° C. in a dry ice-acetonitrile bath was added sodium bis(trimethylsilyl) amide (65.0 mL, 1 M in THF, 65.0 mmol) over 30 minutes. After 45 minutes, a solution of 32.43 g (200 mmol) of carbonyldiimidazole in 150 mL of THF and 100 mL of DMF was added. The mixture was stirred for 2.5 hours at −40° C. and 18 hours at room temperature. The reaction was quenched by adding a solution of 0.5 M $NaH_2PO_4$ (500 mL). The product was isolated by extraction of the reaction mixture with ethyl acetate. The extract was dried with $MgSO_4$ and concentrated to give the crude product, which was purified by flash chromatography using 40–60% acetone/hexanes, yielding 46 g (100%) of the title compound. MS (APCI) m/z 934 $[M+H]^+$.

Step 1f, Compound 11a of Scheme 3, $R^p$ is acetyl, m is 2, A is NH, $X^2$ is H

The compound from Step 1e (25 g, 26.8 mmol) and ethylenediamine (18 mL, 10 eq., 0.27 mol) in 60 mL $CH_3CN$, 10 mL THF and 5 mL water were heated at 70° C. for 6 hours. Solvents were evaporated off, and the residue was taken up in ethyl acetate, which was washed with $NaHCO_3$, brine, dried over $MgSO_4$, and concentrated. This material was used without further purification. MS (ESI) m/z 926 $[M+H]^+$.

Step 1g. Compound 12a of Scheme 3, $R^p$ is acetyl, m is 2, A is NH, B is —C(O)—$(CH_2)q$—, q is 0, D is 1,3-phenylene, $X^1$ is iodo A sample of compound from Step 1f (3.0 g, 3.19 mmol), 3-iodobenzoic acid (1.20 g, 4.81 mmol), 1-hydroxybenzotriazole hydrate (HOBT, 0.65 g, 4.81 mmol), and N-methylmorpholine (0.71 g, 7.02 mmol) were dissolved in $CH_2Cl_2$ (5.0 mL). To the stirred solution at 0° C. was added 1-(3-dimethylaminopropyl)-3-ethylcarbodiimide hydrochloride (0.95 g, 4.81 mmol). After stirring at from 0° C. to room temperature for 3 hours, the mixture was diluted with $CH_2Cl_2$, and the organic layer was washed with water, $NaHCO_3$ and brine. The solvent was removed, and the crude product was purified by chromatography on silica gel with 1:2 to 1:1 acetone/hexanes to give 2.50 g of product as a white foam (67.0%). MS (APCI) m/z 1156 $[M+H]^+$.

Step 1h. Compound of Formula (I), $R^p$ is acetyl, m is 2, A is NH, B is —C(O)—$(CH_2)_q$—, q is 0, D is 1,3-phenylene, E is —$(CH_2)_r$—CH=CH—, r is 0, n is 1

To a solution of the compound from Step 1g (1.16 g, 1.0 mmol) in acetonitrile (100 mL) were added palladium acetate (67.5 mg, 0.30 mmol), tri-(o-tolyl)phosphine (137 mg, 0.45 mmol) and triethylamine (0.278 mL, 2.0 mmol). The mixture was degassed with $N_2$ for 30 minutes, sealed in a tube under nitrogen, and heated at 60° C. for 1 hour and 70 hours at 80° C. The solvent was evaporated off, residue was taken up in ethyl acetate, which was washed with saturated $NaHCO_3$ and brine, dried over $MgSO_4$ and concentrated. The crude product was purified by chromatography on silica gel eluting with acetone/hexanes (1:2 to 2:1) to give 0.799 g of product as light yellow foam. MS (APCI) m/z 1028 $[M+H]^+$.

Step 1i. Compound of Formula (I), 2'-$R^p$ is H, 4"-$R^p$ is acetyl, m is 2, A is NH, B is —C(O)—$(CH_2)_q$—, q is 0, D is 1,3-phenylene, E is —$(CH_2)_r$—CH=CH—, r is 0, n is 1

A sample of the compound from Step 1h (50 mg, 0.049 mmol) in methanol (5 mL) was heated at reflux for 4 hours to remove the 2'-acetyl group. Methanol was evaporated off, and the crude product was purified by chromatography on silica gel eluted with $CH_2Cl_2/MeOH/NH_4OH$ (15:1:0.05) to give the title compound (43 mg, 89%). MS (APCI) m/z 986 $[M+H]^+$.

EXAMPLE 2

Compound of Formula (I), 2'-$R^p$ is H, 4"-$R^p$ is H, m is 2, A is NH, B is —C(O)—$(CH_2)_q$—, q is 0, D is 1,3-phenylene, E is —$(CH_2)_r$—CH=CH—, r is 0, n is 1

A sample of the product from Example 1 (0.15 g, 0.146 mmol) was treated with 1 N LiOH (1.0 mL, ca. 7 eq.) in methanol (5 mL) at room temperature for 8 hours. 1 N hydrochloric acid was added to bring the pH to near neutral. After partial removal of methanol, the reaction mixture was diluted with $CH_2Cl_2$. The two layers were separated, and the organic layer was dried over MgSO4, filtered and concentrated. Crude product was purified by chromatography on silica gel eluted with $CH_2Cl_2/MeOH/NH_4OH$ (10:1:0.05) to give the title compound. MS (APCI) m/z 944 $[M+H]^+$.

EXAMPLE 3

Compound of Formula (I), 2'-$R^p$ is H, 4"-$R^p$ is acetyl, m is 2, A is NH, B is —C(O)—$(CH_2)_q$—, q is 0, D is 1,2-phenylene, E is —$(CH_2)_r$—CH=CH—, r is 0, n is 1

Following the procedures of Example 1, Steps g and h, except substituting 2-iodobenzoic acid for the 3-iodobenzoic acid of Step 1g, and purifying the intermediate by chromatography, two intermediate compounds were obtained (Compounds A and B). Intermediate Compound A was treated according to the procedure of Example 1 Step i, and the title compound was obtained: MS (APCI) m/z 986 $[M+H]^+$.

EXAMPLE 4

Compound of Formula (I), 2'-$R^p$ is H, 4"-$R^p$ is H, m is 2, A is NH, B is —C(O)—$(CH_2)_q$—, q is 0, D is 1,2-phenylene, E is —$(CH_2)_r$—CH=CH—, r is 0, n is 1

Following the procedures of Example 2, except substituting the compound from Example 3 for the compound from Example 1, Step 1i, the title compound was prepared. MS (APCI) m/z 944 $[M+H]^+$. HRMS $C_{50}H_{78}N_3O_{14}$: Calcd. 944.5478; Measured 944.5484.

EXAMPLE 5

Compound of Formula (I), 2'-$R^p$ is H, 4"-$R^p$ is acetyl, m is 2, A is NH, B is —C(O)—$(CH_2)_q$—, q is 1, D is 1,2-phenylene, E is —$(CH_2)_r$—CH=CH—, r is 0, n is 1

Following the procedures of Example 1, steps g, h and i, except substituting 2-bromophenylacetic acid for the 3-iodobenzoic acid of Step Ig, the title compound was prepared. MS (APCI) m/z 1000 $[M+H]^+$.

EXAMPLE 6

Compound of Formula (1), 2'-$R^p$ is H, 4"-$R^p$ is H, m is 2, A is NH, B is —C(O)—$(CH_2)_q$—, q is 1, D is 1,2-phenylene, E is —$(CH_2)_r$—CH=CH—, r is 0, n is 1

Following the procedures of Example 2, except substituting product from Example 5 for the product from Example 1, Step 1i, the title compound was prepared. MS (APCI) m/z 958 $[M+H]^+$.

EXAMPLE 7

Compound of Formula (I), 2'-$R^p$ is H, 4"-$R^p$ is acetyl, m is 0, A is absent, B is —N=CH—, D is 1,2-phenylene, E is —$(CH_2)_r$—CH=CH—, r is 0, n is 1

Step 7a: Compound 11a of Scheme 3, 2'-$R^p$ is H, 4"-$R^p$ is acetyl, m is 0, A is NH, $X^2$ is H To a solution of the compound from Example 1, Step 1e (15 g, 16.1 mmol) in acetonitrile (100 mL) was added hydrazine (2.54 mL, 80.9 mmol), and the solution was stirred at ambient temperature for 48 hours. The solvent was removed in vacuo to give 15.4 g of yellow foam. The residue was purified by column chromatography (95:5:1 dichloromethane:methanol: ammonium hydroxide) followed by recrystalization in acetonitile to give a white foam.

Step 7b: Compound 11a of Scheme 3, 2'-$R^p$ is H, 4"-$R^p$ is acetyl, m is 0, A is absent, B is —N=CH—, D is 1,2-phenylene, $X^1$ is iodo The compound from Step 7a (0.25g, 0.292 mmol), 4Å molecular sieves (1 g) and 2-iodobenzaldehyde (2.92 mmol) were dissolved in toluene (5 mL) and heated under nitrogen at 90° C. for 10 days. The slurry was filtered and purified by column chromatography (95:5:1 $CH_2Cl_2$:MeOH:$NH_4OH$) to give 0.138 g (44%) of white foam.

Step 7c: Compound of Formula (I), 2'-$R^p$ is H, 4"-$R^p$ is acetyl, m is 0, A is absent, B is —N=CH—, D is 1,2-phenylene, E is —$(CH_2)$r—CH=CH—, r is 0, n is 1

To a solution of the compound from Step 7b (0.20 g, 0.175 mmol) in acetonitrile (18 mL) were added palladium acetate (12 mg, 0.053 mmol), tri-(o-tolyl)phosphine (16 mg, 0.053 mmol) and triethylamine (30 mg, 0.35 mmol). The mixture was degassed with $N_2$ for 30 minutes, sealed in a tube under nitrogen, and heated at 60° C. for 1 hour and 70 hours at 80° C. Solvent was evaporated off, and the residue was taken up in ethyl acetate, which was washed with saturated $NaHCO_3$ and brine, dried over $MgSO_4$ and concentrated. The crude product was purified by chromatography on silica gel eluting with acetone/hexanes (1:2 to 2:1) to give pure product (56.6%) as light yellow foam. MS (APCI) m/z 942 $[M+H]^+$.

EXAMPLE 8

Compound of Formula (I), 2'-$R^p$ is H, 4"-$R^p$ is acetyl, m is 0, A is NH, B is —$(CH_2)_q$—, q is 1, D is 1,2-phenylene, E is —$(CH_2)_r$—CH=CH—, r is 0, n is 1

Step 8a: Compound 11a of Scheme 3, 2'-$R^p$ is H, 4"-$R^p$ is acetyl, m is 0, A is NH, B is —$(CH_2)_q$, q is 1, D is 1,2-phenylene, $X^1$ is iodo To a solution of the compound from Example 7, Step 7b (0. 109g) in methanol (5 mL), was added acetic acid (0.1 mL) and $NaBH_3CN$ (68 mg, 1.08 mmol). The solution was stirred at reflux for 18 hours, quenched with saturated $NaHCO_3$ (20 mL), diluted with ethyl acetate (20 mL), then washed with water (20 mL), brine (20 mL), dried $Na_2SO_4$, concentrated in vacuo, and purified by column chromatography (95:5:1 $CH_2Cl_2$:MeOH:$NH_4OH$) to give 0.091 g (78%) of white foam.

Step 8b: Compound 14a of Scheme 3, 2'-$R^p$ is H, 4"-$R^p$ is acetyl, m is 0, A is NH, B is —$(CH_2)_q$, q is 1, D is 1,2-phenylene Following prodedures of Example 7, Step 7c, except substituting the compound from Step 8a for the compound from Step 7b, the title compound is obtained.

Step 8c: Compound 14a of Scheme 3, 2'-$R^p$ is H, 4"-$R^p$ is H, m is 0, A is NH, B is —$(CH_2)_q$—, q is 1, D is 1,2-phenylene Following the procedure of Example 2, except substituting product from Example 8, Step 8b for product from Example 1, Step 1i, the title compound is prepared.

EXAMPLE 9

Compound of Formula (I), 2'-$R^P$ is H, 4"-$R^P$ is acetyl, m is 0, A is NH, B is —$(CH_2)_q$—, q is 1, D is 1,3-phenylene, E is —$(CH_2)_r$—CH=CH—, r is 0, n is 1

Following the procedures of Example 7, Steps 7a and 7b, except substituting 3-iodobenzaldehyde for the 2-iodobenzaldehyde of Step 7b, and treating the product with $NaBH_3CN$ according to the procedure of Example 8, Step a, then carrying out the Heck reaction as in Example 7 Step c, the title compound was prepared. MS (APCI) m/z 944 [M+H]$^+$.

EXAMPLE 10

Compound of Formula (I), 2'-$R^P$ is H, 4"-$R^P$ is acetyl, m is 2, A is NH, B is —$(CH_2)_q$—, q is 1, D is 1,3-phenylene, E is —$(CH_2)_r$—CH=CH—, r is 0, n is 1

Following the procedures of Example 7, except substituting ethylenediamine for the hydrazine of Step 7a and substituting 3-iodobenzaldehyde for the 2-iodobenzaldehyde of Step 7b, then treating the product with $NaBH_3CN$ according to the procedure of Example 8, Step 8a, and carrying out the Heck reaction according to the procedures of Example 7, Step c, the title compound was prepared. MS (ESI) m/z 972 [M+H]$^+$.

EXAMPLE 11

Compound of Formula (I), 2'-$R^P$ is H, 4"-$R^P$ is H, m is 2, A is NH, B is —$(CH_2)_q$—, q is 1, D is 1,3-phenylene, E is —$(CH_2)_r$—CH=CH—, r is 0, n is 1

Treating the compound from Example 10 according to the procedures of Example 1, Step j, and Example 2, the title compound was prepared. MS (ESI) m/z 930 [M+H]$^+$.

EXAMPLE 12

Compound of Formula (II), $R^P$ is H, m is 2, A is —O—, B is —$(CH_2)_q$—, q is 1, D is 1,2-phenylene, E is —$(CH_2)_r$—CH=CH—, r is 0, n is 1

Step 12a. Compound 8 from Scheme 2. Rp is H

To a suspension of the compound prepared in Example 1, Step 1c (7.73 g, 10.0 mmol) in ethanol (25 mL) and water (75 mL) was added aqueous 1 M HCl (18 mL) over 10 minutes. The reaction mixture was stirred for 9 hours at ambient temperature and then was left standing in the refrigerator overnight. Aqueous 2 M NaOH (9 mL, 18 mmol) which resulted in the formation of a white precipitate. The mixture was diluted with water and filtered. The solid was washed with water and dried under vacuum to give the desladinosyl compound 7 (3. 11 g).

Step 12b. Compound 8 from Scheme 2, $R^P$ is benzoyl

To a solution of the product of Step 12a (2.49 g, 4.05 mmol) in dichloromethane (20 mL) was added benzoic anhydride (98%, 1.46 g, 6.48 mmol) and triethylamine (0.90 mL, 6.48 mmol) and the white suspension was stirred for 26 hours at ambient temperature. Aqueous 5% sodium carbonate was added and the mixture was stirred for 20 minutes. The mixture was extracted with dichloromethane. The organic phase was washed with aqueous 5% sodium bicarbonate and brine, dried over sodium sulfate and concentrated in vacuo to give a white foam. Chromatography on silica gel (30% acetone-hexanes) gave the title compound (2.46 g) as a white solid.

Step 12c. Compound 9 from Scheme 2, $R^P$ is benzoyl

To a –10° C. solution under $N_2$ of N-chlorosuccinimide (0.68 g, 5.07 mmol) in dichloromethane (20 mL) was added dimethylsulfide (0.43 mL, 5.92 mmol) over 5 minutes. The resulting white slurry was stirred for 20 minutes at –10° C. and then a solution of the compound resulting from step 12b (2.43 g, 3.38 mmol) in dichloromethane (20 mL) was added and the reaction mixture was stirred for 30 minutes at –10 to –5° C. Triethylamine (0.47 mL, 3.38 mmol) was added dropwise over 5 minutes and the reaction mixture was stirred for 30 minutes at 0° C. The reaction mixture was extracted with dichloromethane. The organic phase was washed twice with aqueous 5% sodium bicarbonate and once with brine, dried over sodium sulfate, and concentrated in vacuo to give a white foam. Chromatography on silica gel (30% acetone-hexanes) gave the title compound (2.27 g) as a white foam.

Step 12d. Compound 10b from Scheme 2, $R^P$ is benzoyl

Following the procedure of Example 1, Step e above, except substituting the compound from Step 12c for the compound from Example 1, Step d, the title compound was prepared.

Step 12e. Compound 12b from Scheme 3, $R^P$ is benzoyl, m is 2, A is —O—, B is —$(CH_2)_q$—, q is 1, D is 1,2-phenylene, X is iodo The compound from Step 12d (1.13 g 1.42 mmol) and 2-((2-iodophenyl)methoxy)ethylamine (1.18 g (4.26 mmol) were dissolved in 3 mL of 10% aqueous $CH_3CN$ and stirred under nitrogen at 60° C. for 20 hours. The mixture was diluted with dichloromethane and quenched with 50 mL of 5% $KH_2PO_4$. The organic layer was washed with brine and dried over $Na_2SO_4$. The solvent was removed, and the residue was chromatographed on silica gel, eluting with 25% acetone in hexanes to give the title compound.

Step 12f. Compound 14b from Scheme 3, $R^P$ is benzoyl, m is 2, A is A is —O—, B is —$(CH_2)_q$—, q is 1, D is 1,2-phenylene To a solution of the compound from Step 12e (0.75 g, 0.948 mmol) in acetonitrile (50 mL) were added palladium acetate (85 mg, 0.379 mmol), tri-(o-tolyl)phosphine (228 mg, 0.750 mmol) and triethylamine (0.50 mL, 3.687 mmol). The mixture was degassed with $N_2$ for 30 minutes, sealed in a tube under nitrogen, and heated for 16 hours at 50° C. Solvent was evaporated off, and residue was taken up in ethyl acetate, which was washed with saturated $NaHCO_3$ and brine, then dried over $MgSO4$. The solvents were removed and the crude product was purified by chromatography on silica gel eluting with 1:4:1 to 1:3:1 acetone/hexanes/t-butanol to give 332 mg of the title compound.

Step 12g. Compound of Formula (II), $R^P$ is H, m is 2, A is —O—, B is —$(CH_2)_q$—, q is 1, D is 1,2-phenylene, E is —$(CH_2)_r$—CH=CH—, r is 0, n is 1

A solution of the compound from Step 12g (50 mg) in methanol was stirred for 2 days. The solvent was removed, and the product was purified by chromatography on silica gel, eluting with 5% methanol in dichloromethane containing 0.5% $NH_4OH$ to give the title compound (29 mg). MS (APCI) m/z 771 [M+H]$^+$.

EXAMPLE 13

Compound of Formula (I), $R^P$ is acetyl, m is 2, A is —O—, B is absent, D is 3,4-quinolene, E is —$(CH_2)_r$—CH=CH—, r is 0, n is 1

Step 13a. Compound 11a from Scheme 3, m is 2, A is —O—, $X^2$ is H

To a solution of imidazolide (compound 10a of Scheme 3, 15 g, 16.6 mmol) in acetonitrile (200 mL) and water (20 mL), was added 2-amino-ethanol (6.91 g, 113 mmol). The solution was stirred at ambient temperature for 48 hours. The solvent was removed in vacuo, and the material purified by FSC (95:5:0.1 $CH_2Cl_2$:MeOH:$NH_4OH$), then recrystalized from acetonitrile to give 8.7 g (56%) of white foam. MS (ESI) m/z 927 $[M+H]^+$.

Step 13b. Compound 12a from Scheme 3, m is 2, A is —O—, B is absent, D is 3,4-quinolene, $X^1$ is I To a slurry of the compound from Step 13a (2.5 g, 2.70 mmol), 2-iodo-3-hydroxyquinoline (0.74 g, 2.72 mmol), and triphenylphosphine (1.06 g, 4.72 mmol) in THF (40 mL), was added DEAD (0.74 mL, 4.72 mmol). The solution quickly became homogenous and was stirred for 18 hours. The solution was quenched with saturated sodium bicarbonate, and the solvent removed in vacuo. The residue was dissolved in ethyl acetate (75 mL), washed with saturated sodium bicarbonate (50 mL), water (50 mL), brine (50 mL), dried over sodium sulfate, and concentrated in vacuo. The yellow foam was purified by MPLC (95:5:0.1 $CH_2Cl_2$:MeOH:$NH_4OH$). A second purification by MPLC (7:3:0.1 Acetone:Hexane:triethyl amine) afforded 2.96 g (93%) of white foam. (ESI) m/z 1178 $[M+H]^+$.

Step 13c. Compound of Formula (I), $R^p$ is acetyl, m is 2, A is —O—, B is absent, D is 3,4-quinolene, E is —$(CH_2)_r$—CH=CH—, r is 0, n is 1

The compound from Step 15b was treated by the method of Example 1, Step g to afford the title compound. (ESI) n/z 1010 $[M+H]^+$

EXAMPLE 14

Compound of Formula (I), $R^p$ is acetyl, m is 1, A is absent, B is absent, D is absent, E is —$(CH_2)_r$—CH=CH—, r is 0, n is 1

Step 14a. Compound 11a from Scheme 3, $R^p$ is acetyl, m is 1, A is absent, $X^2$ is —CH=CH—H The compound from Example 1 Step e (compound 10a of Scheme 3, 25 g, 26.8 mmol) and allylamine (15 mL) in 50 mL and 5 mL water were heated at 70° C. for 6 hours. Solvents were evaporated off, and the residue was taken up in ethyl acetate, which was washed with $NaHCO_3$, brine, dried over $MgSO_4$, and concentrated. The crude product was purified by chromatography on silica gel eluted with acetone/hexanes from 1:2 to 1:1 to give the desired product (15 g, 60.7%). The product was futher purified by recrystalization from ethylacetate. MS (ESI) m/z 926 $[M+H]^+$.

Step 14b. Compound of Formula (I), $R^p$ is acetyl, m is 1, A is absent, B is absent, D is absent, E is —$(CH_2)_r$—CH=CH—, r is 0, n is 1

The solution of the compound from step 14a (2.50 g, 2.71 mmol) and Bis(tricyclohexylphosphine)benylidine ruthenium (IV) dichloride (Grubbs catalyst, 0.25 g) in dichloromethane (500 mL) was stirred at room temperature under nitrogen for 24 hrs.

Solvent was evaporated, the black residual material was purified by chromotagraphy on silica gel eluted with acetone/hexanes from 1:2 to 2:1 to give product (2.36 g, 97.4%).

Step 14c. Compound of Formula (I), $R^p$ is H, m is 1, A is absent, B is absent, D is absent, E is —$(CH_2)_r$—CH=CH—, r is 0, n is 1

The solution of the compound from Step 14b (75 mg) in methanol (2 mL) was heated at refluxing for 3 hrs to remove the acetyl group at C2'. The cooled solution was then treated with LiOH (0.9 mL) at r.t. for 5 hrs to remove the acetyl group at C4" position. After neutralization with 1 N HCl, the mixture was extracted with AcOEt twice. Combined extract was dried over $MgSO_4$, concentrated and purified by silica gel gravity column, eluting with 10% MeOH in methylene chloride containing 0.5% ammonium hydroxide, to give 55 mg (57%) of the title compound. MS (APCI) m/z 811 $[M+H]^+$. HRMS Calcd for $C_{42}H_{71}N_2O_{13}$, 811.4856; measured, 811.4968. NMR $^{13}C$ (CDCl3) $\delta$216.1, 167.8, 157.6, 130.4, 130.1, 103,0, 95.4, 83.9, 80.3, 77.9, 77.2, 75.0, 72.7, 70.6, 69.1, 65.7, 20 65.6, 56.0, 55.4, 49.5, 45.4, 45.2, 42.3, 40.2, 39.2, 38.7, 38.4, 34.6, 30.8, 28.5, 22.9, 21.5, 21.4, 20.2, 18.5, 17.5, 14.2, 13.4, 13.2, 11.2, 8.50.

EXAMPLE 15

Compound of Formula (I), $R^p$ is H, m is 3, A is absent, B is absent, D is absent, E is absent, n is 1

A sample of the compound from Example 16 (25 mg) was hydrogenated with hydrogen (1 atm) and 10% palladium on carbon (10 mg) in ethanol. The catalyst was removed by filtration, and the filtrate was concentrated and purified by silica gel gravity column, eluting with 10% MeOH in methylene chloride containing 0.5% ammonium hydroxide, to give 24 mg (96%) of the title compound. (APCI) m/z 813 $[M+H]^+$. HRMS Calcd for $C_{42}H_{73}N_2O_{13}$, 813.5113; measured, 813.5120.

EXAMPLE 16

Compound of Formula (II), $R^p$ is H, m is 1, A is absent, B is absent, D is absent, E is —$(CH_2)_r$—CH=CH—, r is 0, n is 1

A sample of the compound from Example 14 Step b (1.25 g, 1.40 mmol) was treated with 2 N hydrochloric acid (18 mL) in EtOH (15 mL) for a total of 120 hours. The mixture was neutralized with 2 N NaOH, then extracted with $CH_2Cl_2$ twice. Combined $CH_2Cl_2$ extracts were dried over $MgSO_4$ and concentrated. Crude product was purified by flash chromatography on silica gel eluted with acetone/hexanes 1:1 to 2:1 to give the intermediate C-3 hydroxyl compound (0.65 g, 81.2%) along with 0.21 g of unreacted starting material (16.8%).

To a -10° C. solution under $N_2$ of N-chlorosuccinimide (0.173 g, 1.30 mmol) in dichloromethane (3 mL) was added dimethylsulfide (0.12 mL, 1.63 mmol) over 5 minutes. The resulting white slurry was stirred for 20 minutes at -10° C. and then a solution of the intermediate C-3 hydroxyl compound (0.45 g, 0.65 mmol) in dichloromethane (2 mL) was added and the reaction mixture was stirred for 30 minutes at –10 to –5° C. Triethylamine (0.23 mL, 1.63 mmol) was added dropwise over 5 minutes, and the reaction mixture was stirred for 30 minutes at 0° C. The reaction mixture was extracted with dichloromethane. The organic phase was washed twice with aqueous 5% sodium bicarbonate and once with brine, dried over sodium sulfate, and concentrated in vacuo to give a white foam (370 mg). This second intermediate was heated in methanol for 4 hours to remove the acetyl group at C-2' position. Solvent was evaporated off, and the residue was purified by silica gel chromatography, eluting with 5% MeOH in methylene chloride containing 0.5% ammonium hydroxide, to give the title compound (301 mg, 71.4% yield for two steps). MS (APCI) m/z 651 $[M+H]^+$. HRMS Calcd for $C_{34}H_{54}N_2O_{10}$, 651.3857; measured, 651.3843.

EXAMPLE 17

Compound of Formula (I), $R^p$ is H, m is 2, A is absent, B is absent, D is absen, E is —$(CH_2)_r$—CH=CH—, r is 0, n is 1

Step 17a. Compound 11a from Scheme 3, m is 1, A is absent, $X^2$ is —$CH_2$—CH=CH—H The 11-N homoallyl cyclic carbamate was prepared from the compound of Example 1 Step e (compound 10a of Scheme 3, 1.0 g, 0.931 mmol) following procedures described in Step 16a, except except substituting homoallylamine (3-butenamine, 2.0 g, ca. 20 equiv., prepared as described by Koziara et al., *Synthesis*, 1984, 202–204) for allylamine, in 55% yield. MS (ESI) m/z 937 [M+H]$^+$. HRMS Calcd for $C_{49}H_{81}N_2O_{15}$, 937.5361; measured, 937.5636.

Step 17b. Compound of Formula (I), R$^p$ is acetyl, m is 2, A is absent, B is absent, D is absent, E is —(CH$_2$)$_r$—CH=CH—, r is 0, n is 1

The solution of the compound from step 17a was treated according to the procedure of Example 14b to give the title compound. MS (ESI) m/z 909 [M+H]$^+$. HRMS Calcd for $C_{47}H_{77}N_2O_{15}$, 909.5324; measured, 909.5342.

Step 17c. Compound of Formula (I), R$^p$ is H, m is 2, A is absent, B is absent, D is absent, E is —(CH$_2$)$_r$—CH=CH—, r is 0, n is 1

The solution of the compound from step 17b was hydrolyzed according to the procedure of Example 14c to give the title compound. MS (ESI) m/z 825 [M+H]$^+$.

EXAMPLE 18

Compound of Formula (II), R$^p$ is H, m is 2, A is absent, B is absent, D is absent, E is —(CH$_2$)$_r$—CH=CH—, r is 0, n is 1

Step 18a. Compound 12b of Scheme 3, R$^p$ is H, m is 2, A is absent, B is absent, D is absent The cladinose moiety was removed from the compound of Step 17a (265 mg) with 3.0 mL of 2 N HCl and 3.0 mL of EtOH following procedures described previously to give the 3-hydroxy intermediate compound.

To a –10° C. solution under N2 of N-chlorosuccinimide (57 mg, 0.427 mmol) in dichloromethane (2 mL) was added dimethylsulfide (37 mL, 0.704 mmol). The resulting white slurry was stirred for 20 minutes at –10° C. and then a solution of the 3-hydroxy intermediate compound (120 mg, 0.163 mmol) in dichloromethane (1 mL) was added, and the reaction mixture was stirred for 30 minutes at –10° C. to –5° C. Triethylamine (71 mL, 0.509 mmol) was added dropwise, and the reaction mixture was stirred for 30 minutes at 0° C. The reaction mixture was extracted with dichloromethane. The organic phase was washed twice with aqueous 5% sodium bicarbonate and once with brine, dried over sodium sulfate, and concentrated in vacuo to give a white foam. Chromatography on silica gel (30% acetone-hexanes) gave the title compound (70 mg, 60.8%) as a white foam. MS (APCI) m/z 735 [M+H]$^+$.

Step 18b. Compound 12b of Scheme 3, R$^p$ is H, m is 2, A is absent, B is absent, D is absent Following the procedure of Example 16 Step b, the compound from Step 18a (70 mg, 0.256 mmol) was treated with Ruthenium catalyst (15 mg) in CH$_2$Cl$_2$ (40 mL) to give 64 mg of title compound after purification. MS (ESI) m/z 707 [M+H]$^+$.

Step 1 8d. Compound of Formula (II), R$^p$ is H, m is 2, A is absent, B is absent, D is absent, E is —(CH$_2$)$_r$—CH=CH—, r is 0, n is 1

The compound from Step 18b was treated with in hot methanol followed by purification on silica gel gravity column, eluting with 5% MeOH in methylene chloride containing 0.5% ammonium hydroxide, to give title compound (36 mg, 60% yield). MS (ESI) m/z 665 [M+H]$^+$.

EXAMPLE 19

Compound of Formula (I), R$^p$ is H, m is 1, A is absent, B is —CHOH—(CH2)$_q$—, q is 1, D is absent, E is —(CH$_2$)$_r$—CH=CH—, r is 0, n is 1

Step 19a. Compound 11a from Scheme 3, m is 1, A is absent, X$^2$ is —C(O)—, (CH2)$_q$—H, q is 0

To a solution of oxalyl chloride (0.68 mL, 7.85 mmol) in dichloromethane (30 mL) cooled to –78° C. was added DMSO (1.11 mL, 15.7 mmol) in dichloromethane (10 mL). The solution was stirred for 10 minutes then the compound from Example 13 Step a (4.85 g, 5.23 mmol) in dichloromethane (30 mL) cooled to –78° C. was added via a cannula. The solution was stirred at –78° C. for 3 hours, then quenched with triethylamine (3.65 mL, 26.2) and warmed to ambient temperature. The solution was diluted with dichloromethane (30 mL), washed with water (75 mL), brine (75 mL), dried over sodium sulfate, and concentrated in vacuo to give 4.7 g of white foam (97%) used without further purification. MS (ESI) n/z 925 [M+H]$^+$.

Step 19b. Compound 12a from Scheme 3, m is 1, A is absent, B is absent, D is —CH(OH)—CH$_2$—CH=CH2, X$^1$ is H To a two phase solution of the compound from Step 19a (1.2 g, 1.30 mmol) and allyl bromide (0.63 g, 5.19 mmol) in THF (10 mL) and saturated ammonia chloride (25 mL) was added zinc dust (0.34 g, 5.19 mmol) all at once. The solution was vigorously stirred for 4 hours, diluted with ethyl acetate (100 mL), washed with water (2×50 mL), brine (50 mL), dried over sodium sulfate, and concentrated in vacuo. The material was purified by FSC (95:5:0.1 CH$_2$Cl$_2$:MeOH:NH$_4$OH), to give 0.99 g (78.6%) of white foam. MS (ESI) m/z 967 [M+H]$^+$.

Step 19c. Compound of Formula (I), R$^p$ is H, m is 1, A is absent, B is —CHOH—(CH2)$_q$—, q is 1, D is absent The compound of Step 19b was treated with Grubbs catalyst according to the procedure of Example 14b, then the acetyl protecting groups were removed by further treatment with hot methanol and LiOH according to the procedures of Example 1, step i and Example 2 to give the title compound. MS (ESI) m/z 855 [M+H]$^+$. HRMS Calcd for $C_{44}H_{75}N_2O_{14}$, 855.5213; measured, 855.5212.

EXAMPLE 20

Compound of Formula (I), R$^p$ is acetyl, m is 1, A is absent, B is —C(O)—(CH$_2$)$_q$—, q is 1, D is absent, E is —(CH$_2$)$_r$—CH=CH—, r is 0, n is 1

Step 20a. Compound of Formula (1), R$^p$ is acetyl, m is 1, A is absent, B is —C(O)—(CH$_2$)$_q$—, q is 1, D is absent, E is —(CH$_2$)$_r$—CH=CH—, r is 0, n is 1

The compound of Step 19c was oxidized with Swern reagents according to the procedure of Example 19a to give the title compound. MS (ESI) n/z 895 [M+H]$^+$.

Step 20b. Compound of Formula (I), R$^p$ is H, m is 1, A is absent, B is —C(O)—(CH$_2$)$_q$—, q is 1, D is absent, E is —(CH$_2$)$_r$—CH=CH—, r is 0, n is 1

The compound 20a was hydrolyzed by further treatment with hot methanol and LiOH according to the procedures of Example 1, step i and Example 2 to give the title compound. MS (ESI) m/z 853 [M+H]$^+$.

EXAMPLE 21

Compound of Formula (II), R$^p$ is H, m is 2, A is —NH—, B is —C(O)—(CH$_2$)$_q$—, q is 0, D is 1,2-phenylene, E is —(CH$_2$)$_r$—CH=CH—, r is 0, n is 1

A sample of the compound of Example 3 (200 mg, 0.195 mmol) was treated with 2 N hydrochloric acid (4 mL) in EtOH (6 mL) for a total of 40 hours. The mixture was neutralized with 2 N NaOH, extracted with CH2Cl2 twice. Combined CH2Cl2 extract was dried over MgSO4 and concentrated. Crude product was purified by flash chromatography on silica gel eluted with CH$_2$Cl$_2$/MeOH/NH$_4$OH (10:1:0.05) to give the intermediate C-3 hydroxyl compound (73.5 mg, 45.6%).

To a −10° C. solution under $N_2$ of N-chlorosuccinimide (28 mg, 0.211 mmol) in dichloromethane (1 mL) was added dimethylsulfide (18.6 μL, 0.254 mmol). The resulting white slurry was stirred for 20 minutes at −10° C. and then a solution of the intermediate C3-hydroxyl compound (70 mg, 0.0845 mmol) in dichloromethane (1 mL) was added, and the reaction mixture was stirred for 30 minutes at −10 to −5° C. Triethylamine (35.4 μL, 0.254 mmol) was added dropwise, and the reaction mixture was stirred for 30 minutes at 0° C. The reaction mixture was extracted with dichloromethane. The organic phase was washed twice with aqueous 5% sodium bicarbonate and once with brine, dried over sodium sulfate, then concentrated in vacuo to give a white foam.

The crude product (30 mg) from above was heated in methanol for 4 hours to remove the acetyl group at C-2' to give the title compound (27 mg). MS (ESI) m/z 874 $[M+H]^+$.

EXAMPLE 22

Compound of Formula (I), $R^p$ is H, m is 1, A is absent, B is —CH(OH)—$(CH_2)_q$—, q is 0, D is absent, E is absent, n is 3

Hydrogenation of the compound of Example 19 with $H_2$ over Pd/C gave the title compound. MS (ESI) n/z 857 $[M+H]^+$.

EXAMPLE 23

Compound of Formula (I), $R^p$ is H, m is 1, A is absent, B is —CH(OH)—CH(OH)—$(CH_2)_q$—, q is 0, D is absent, E is absent n is 1

To a stirred solution of the acetyl-protected intermediate compound from Example 14, Step b (900 mg, 0.976 mmol) and N-methyl morpholine N-oxide (120 mg, 1.02 mmol) in a mixed solvents containing acetone/THF/H2O (5/2/1 mL) at 0° C. was added osmium tetraoxide (24 g, 0.094 mmol). The mixture was stirred at 0° C. to r.t for 5 hrs to drive the reaction to completion. After quenching with a solution of NaHSO3, the mixture was partitioned between methylene chloride and water. Organic layer was dried and concentrated to give the acetyl-protected intermediate (920 mg, 99.0%).

A portion of the acetyl-protected intermediate( 20 mg, 0.129 mmol) was heated in methanol (5 mL) for 4 hours at reflux, then the solution was treated with 1 N LiOH (0.8 ml, 7.0 eq.) for 7 hours. The mixture was extracted with methylene chloride twice, combined organic layer was dried over MgSO4, concentrated. Crude product was purified by gravity silica gel column eluted with $CH_2Cl_2/MeOH/NH_4OH$ (10:1:0.05) to give the title compound. MS (ESI) m/z 845 $[M+H]^+$.

EXAMPLE 24

Compound of Formula (I), 2'-$R^p$ is H, 4''-$R^p$ is H, m is 2, A is NH, B is —C(O)—$(CH_2)_q$—, q is 0, D is 1,2-phenylene, E is —$(CH_2)_r$—CH=CH—, r is 1, n is 1

A sample of the compound B from Example 3 (85 mg, 0.083 mmol) in methanol (10 mL) was heated at reflux for 4 hours to remove the 2'-acetyl group. The reaction mixture was cooled to room temperature. The mixture was treated with 1 N LiOH (1.0 mL, ca. 10 eq.) at room temperature for 7 hours. 1 N hydrochloric acid was added to bring the pH to near neutral. After partial removal of methanol, the reaction mixture was diluted with $CH_2Cl_2$. The two layers were separated, and the organic layer was dried over MgSO4, filtered and concentrated. Crude product was purified by chromatography on silica gel eluted with $CH_2Cl_2/MeOH/NH_4OH$ (10:1:0.05) to give the title compound, 74.5 mg, 96.1%. MS (ESI) m/z 944 $[M+H]^+$. HRMS Calcd for $C_{50}H_{78}N_3O_{14}$, 944.5478; measured, 944.5479.

What is claimed is:

1. A compound selected from the group consisting of:

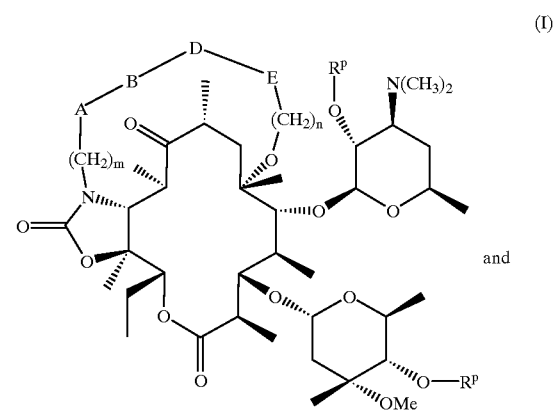

(I)

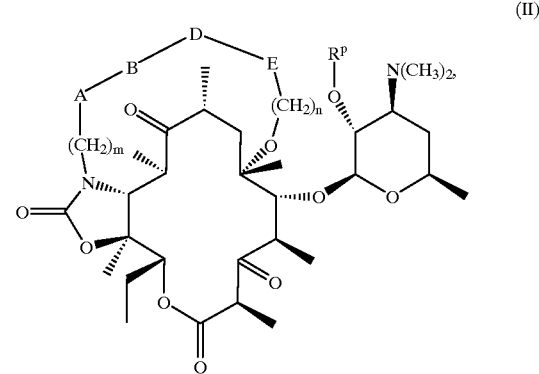

(II)

wherein m is 0, 1, 2, 3, 4, 5, 6 or 7;

n is 0, 1, 2, 3 or 4;

$R^p$ is independently hydrogen or a hydroxy protecting group at each occurrence;

A is absent or is selected from the group consisting of
(1) —O—, and
(2) —N($R^1$)—, wherein $R^1$ is hydrogen or $C_1$–$C_6$-alkyl optionally substituted with aryl or heteroaryl;

B is absent or is selected from the group consisting of
(1) —$(CH_2)_q$—, wherein q is 0, 1, 2, 3, 4, 5, or 6,
(2) —C(O)—$(CH_2)_q$—,
(3) —C(O)—O—$(CH_2)_q$—,
(4) —C(O)—N$R^1$—$(CH_2)_q$—, wherein $R^1$ is as defined previously, and (5) —N=CH—(CH$_2$)$_q$—;
(6) —CH(OH)—(CH$_2$)$_q$—, and
(7) —CH(OH)—CH(OH)—(CH$_2$)$_q$—;

D is absent or is selected from the group consisting of
(1) alkenylene,
(2) arylene,
(3) substituted arylene,
(4) heteroarylene,
(5) substituted heteroarylene;
(6) alkenylene-arylene,
(7) arylene-arylene,
(8) substituted arylene-arylene,
(9) heteroarylene-arylene,
(10) substituted heteroarylene-arylene,
(11) alkenylene-heteroarylene,
(12) arylene-heteroarylene,
(13) substituted arylene-heteroarylene,
(14) heteroarylene-heteroarylene, and
(15) substituted heteroarylene-heteroarylene;

E is absent or is selected from the group consisting of
(1) —(CH$_2$)$_r$—CH=CH—,
(2) —(CH$_2$)$_r$—O—, wherein r is 0, 1, 2, 3 or 4,
(3) —(CH$_2$)$_r$—NR$^1$—CH$_2$—CH(OH)—, wherein R$^1$ is as defined previously,
(4) —(CH$_2$)$_r$—C(O)—O—,
(5) —(CH$_2$)$_r$—N(R$^1$)—,
(6) —(CH$_2$)$_r$—O—C(O)—,
(7) —(CH$_2$)$_r$—C(O)—N(R$^1$)— and
(8) —(CH$_2$)$_r$—N(R$^1$)—C(O)—, with the restrictions that the sum of m +q may not be 0, that the sum of m+n+q+r is an integer from 2 to 7, that when the A and B moieties are both absent then m cannot be 0, that when E is —CH=CH— and the A, B and D moieties are all absent then m cannot be 0, and that B can be —N=CH—(CH$_2$)$_q$— only when A is absent and m is 0.

2. A compound according to claim 1 which is selected from the group consisting of:

Compound of Formula (I), 2'-R$^p$ is H, 4"-R$^p$ is acetyl, m is 2, A is NH, B is —C(O)—(CH$_2$)q—, q is 0, D is 1,3-phenylene, E is —(CH$_2$)r—CH=CH—, r is 0, n is 1;

Compound of Formula (I), 2'-R$^p$ is H, 4"-R$^p$ is H, m is 2, A is NH, B is —C(O)—(CH$_2$)q—, q is 0, D is 1,3-phenylene, E is —(CH$_2$)r—CH=CH—, r is 0, n is 1;

Compound of Formula (I), 2'-R$^p$ is H, 4"-R$^p$ is acetyl, m is 2, A is NH, B is —C(O)—(CH$_2$)q—, q is 0, D is 1,2-phenylene, E is —(CH$_2$)r—CH=CH—, r is 0, n is 1;

Compound of Formula (I), 2'-R$^p$ is H, 4"-R$^p$ is H, m is 2, A is NH, B is —C(O)—(CH$_2$)q—, q is 0, D is 1,2-phenylene, E is —(CH$_2$)r—CH=CH—, r is 0, n is 1;

Compound of Formula (I), 2'-R$^p$ is H, 4"-R$^p$ is acetyl, m is 2, A is NH, B is —C(O)—(CH$_2$)q—, q is 1, D is 1,2-phenylene, E is —(CH$_2$)r—CH=CH—, r is 0, n is 1;

Compound of Formula (1), 2'-RP is H, 4"-R$^p$ is H, m is 2, A is NH, B is —C(O)—(CH$_2$)q—, q is 1, D is 1,2-phenylene, E is —(CH$_2$)r—CH=CH—, r is 0, n is 1;

Compound of Formula (I), 2'-R$^p$ is H, 4"-R$^p$ is acetyl, m is 0, A is absent, B is —N=CH—, D is 1,2-phenylene, E is —(CH$_2$)r—CH=CH—, r is 0, n is 1;

Compound of Formula (I), 2'-R$^p$ is H, 4"-R$^p$ is acetyl, m is 0, A is NH, B is —(CH$_2$)q—, q is 1, D is 1,2-phenylene, E is —(CH$_2$)r—CH=CH—, r is 0, n is 1;

Compound of Formula (I), 2'-R$^p$ is H, 4"-R$^p$ is acetyl, m is 0, A is NH, B is —(CH$_2$)q—, q is 1, D is 1,3-phenylene, E is —(CH$_2$)r—CH=CH—, r is 0, n is 1;

Compound of Formula (I), 2'-R$^p$ is H, 4"-R$^p$ is acetyl, m is 2, A is NH, B is —(CH$_2$)q—, q is 1, D is 1,3-phenylene, E is —(CH$_2$)r—CH=CH—, r is 0, n is 1

Compound of Formula (I), 2'-R$^p$ is H, 4"-R$^p$ is H, m is 2, A is NH, B is —(CH$_2$)q—, q is 1, D is 1,3-phenylene, E is —(CH$_2$)r—CH=CH—, r is 0, n is 1;

Compound of Formula (II), R$^p$ is H, m is 2, A is —O—, B is —(CH$_2$)q—, q is 1, D is 1,2-phenylene, E is —(CH$_2$)r—CH=CH—, r is 0, n is 1;

Compound of Formula (I), R$^p$ is acetyl, m is 2, A is —O—, B is absent, D is 3,4-quinolene, E is —(CH$_2$)r—CH=CH—, r is 0, n is 1;

Compound of Formula (I), R$^p$ is acetyl, m is 1, A is absent, B is absent, D is absent, E is —(CH$_2$)r—CH=CH—, r is 0, n is 1;

Compound of Formula (I), R$^p$ is H, m is 3, A is absent, B is absent, D is absent, E is absent, n is 1;

Compound of Formula (II), R$^p$ is H, m is 1, A is absent, B is absent, D is absent, E is —(CH$_2$)r—CH=CH—, r is 0, n is 1;

Compound of Formula (I), R$^p$ is H, m is 2, A is absent, B is absent, D is absent, E is —(CH$_2$)r—CH=CH—, r is 0, n is 1;

Compound of Formula (II), R$^p$ is H, m is 2, A is absent, B is absent, D is absent, E is —(CH$_2$)r—CH=CH—, r is 0, n is 1;

Compound of Formula (I), R$^p$ is H, m is 1, A is absent, B is —CHOH—(CH2)q-—, q is 1, D is absent, E is —(CH$_2$)r—CH=CH—, r is 0, n is 1;

Compound of Formula (I), R$^p$ is acetyl, m is 1, A is absent, B is —C(O)—(CH2)q—, q is 1, D is absent, E is —(CH$_2$)r—CH=CH—, r is 0, n is 1;

Compound of Formula (II), R$^p$ is H, m is 2, A is —NH—, B is —C(O)—(CH2)q—, q is 0, D is 1,2-phenylene, E is —(CH$_2$)r—CH=CH—, r is 0, n is 1;

Compound of Formula (I), R$^p$ is H, m is 1, A is absent, B is —CH(OH)—(CH$_2$)q—, q is 0, D is absent, E is absent, n is 3;

Compound of Formula (I), R$^p$ is H, m is 1, A is absent, B is —CH(OH)—CH(OH)—(CH$_2$)q—, q is 0, D is absent, E is absent, n is 1; and Compound of Formula (I), 2'-R$^p$ is H, 4"-R$^p$ is H, m is 2, A is NH, B is —C(O)—(CH$_2$)q—, q is 0, D is 1,2-phenylene, E is —(CH$_2$)r—CH=CH—, r is 1, n is 1.

3. A pharmaceutical composition for treating bacterial infections comprising a therapeutically effective amount of a compound of claim 1 or a pharmaceutically acceptable salt or ester thereof in combination with a pharmaceutically acceptable carrier.

4. A method for treating bacterial infections comprising administering to a mammal in need of such treatment a pharmaceutical composition containing a therapeutically-effective amount of a compound of claim 1 or a pharmaceutically acceptable salt or ester thereof.

5. A compound according to claim 1 having the formula (I)

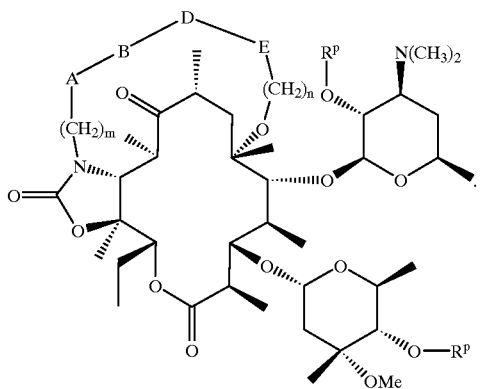

(I)

6. A compound according to claim 5 wherein E is —CH=CH— and n is 1.

7. A compound according to claim 1 having the formula (II)

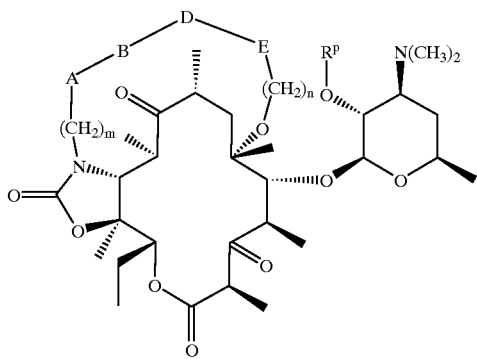

8. A compound according to claim 7 wherein E is —CH=CH— and n is 1.

9. A process for preparing a compound selected from the group consisting of

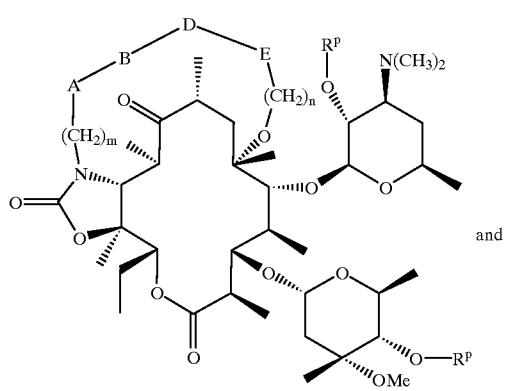

and

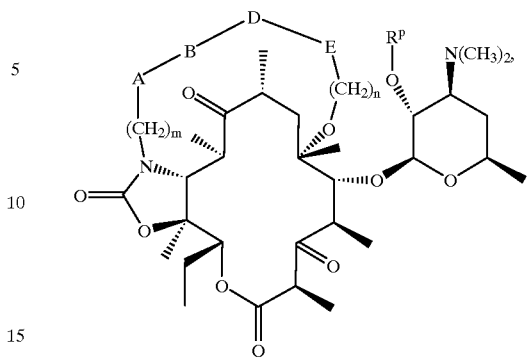

(II)

wherein m is 0, 1, 2, 3, 4, 5, 6 or 7;

n is 0, 1, 2, 3 or 4;

$R^p$ is independently hydrogen or a hydroxy protecting group at each occurrence;

A is absent or is selected from the group consisting of
(1) —O—, and
(2) —N($R^1$)—, wherein $R^1$ is hydrogen or $C_1$–$C_6$-alkyl optionally substituted with aryl or heteroaryl;

B is absent or is selected from the group consisting of
(1) —$(CH_2)_q$—, wherein q is 0, 1, 2, 3, 4, 5, or 6,
(2) —C(O)—$(CH_2)_q$—,
(3) —C(O)—O—$(CH_2)_q$—,
(4) —C(O)—$NR^1$—$(CH_2)_q$—, wherein $R^1$ is as defined previously, and
(5) —N=CH—$(CH_2)_q$—;
(6) —CH(OH)—$(CH_2)_q$—, and
(7) —CH(OH)—CH(OH)—$(CH_2)_q$—;

D is absent or is selected from the group consisting of
(1) alkenylene,
(2) arylene,
(3) substituted arylene,
(4) heteroarylene,
(5) substituted heteroarylene;
(6) alkenylene-arylene,
(7) arylene-arylene,
(8) substituted arylene-arylene,
(9) heteroarylene-arylene,
(10) substituted heteroarylene-arylene,
(11) alkenylene-heteroarylene,
(12) arylene-heteroarylene,
(13) substituted arylene-heteroarylene,
(14) heteroarylene-heteroarylene, and
(15) substituted heteroarylene-heteroarylene;

E is absent or is selected from the group consisting of
(1) —$(CH_2)_r$—CH=CH—,
(2) —$(CH_2)_r$—O—, wherein r is 0, 1, 2, 3 or 4,
(3) —$(CH_2)_r$—$NR^1$—$CH_2$—CH(OH)—, wherein $R^1$ is as defined previously,
(4) —$(CH_2)_r$—C(O)—O—,
(5) —$(CH_2)_r$—N($R^1$)—,
(6) —$(CH_2)_r$—O—C(O)—,
(7) —$(CH_2)_r$—C(O)—N($R^1$)—, and
(8) —$(CH_2)_r$—N($R^1$)—C(O)—, with the restrictions that the sum of m+q may not be 0, that the sum of m+n+q+r is an integer from 2 to 7, that when the A and B moieties are both absent then m cannot be 0, that when E is —CH=CH— and the A, B and D moieties are all absent then m cannot be 0, and that B can be —N═CH—(CH$_2$)$_q$— only when A is absent and m is 0, the method comprising (a) treating a compound having the formula

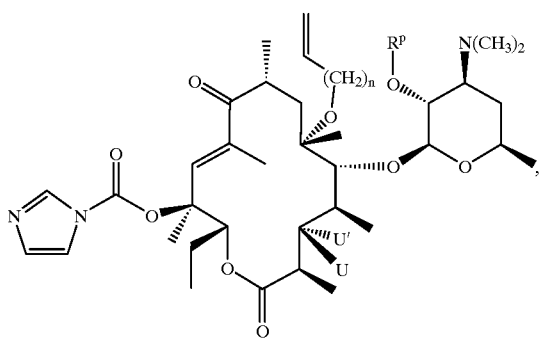

wherein U is 4"-R$^P$-O-cladinose and U' is H, or U and U' taken together with the carbon atom to which they are attached form a carbonyl group, with a reagent compound having the formula H$_2$N—(CH$_2$)$_m$—A—B—D—X$^1$, wherein m, A, B, are as defined previously, D is as defined previously, and X$^1$ is a leaving group selected from the group consisting of Cl, Br, I and trifluoromethanesulfonate, to prepare an intermediate compound having the formula

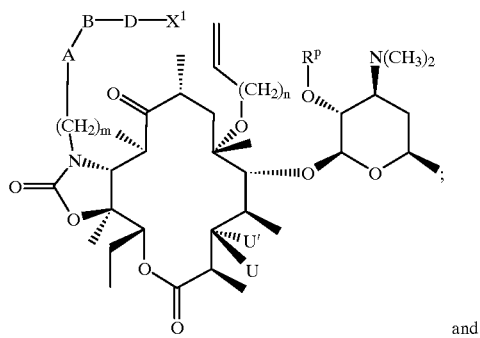

and (b) cyclizing and optionally reducing the compound from Step (a).

10. The process of claim 9 wherein U is 4"-R$^P$-O-cladinose, and the product is a compound of formula (I).

11. The process of claim 9, wherein U and U' are taken together with the carbon atom to which they are attached form a carbonyl group, and the product is a compound of formula (II).

12. The process of claim 11, wherein the reagent of Step (a) is 2-((2-iodophenyl)methoxy)ethylamine.

13. A process for preparing a compound selected from the group consisting of

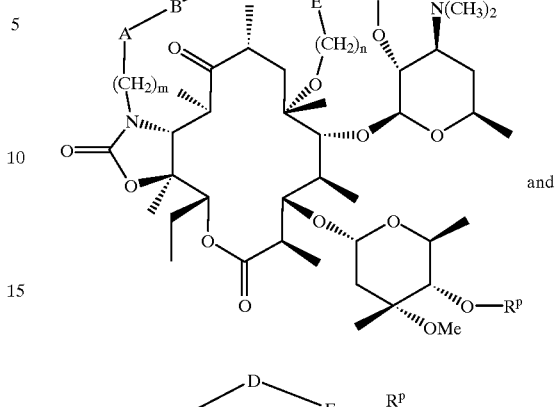

and

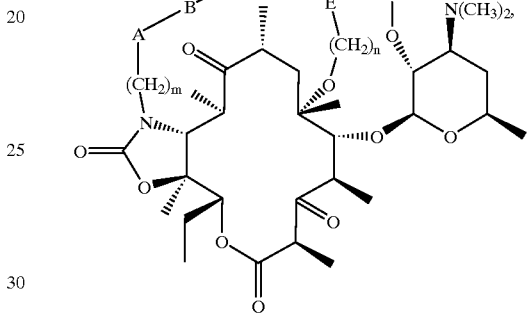

wherein
m is 0, 1, 2, 3, 4, 5, 6 or 7;
n is 0, 1, 2, 3 or 4;
R$^P$ is independently hydrogen or a hydroxy protecting group at each occurrence;
A is absent or is selected from the group consisting of
  (1) —O—, and
  (2) —N(R$^1$)—, wherein R$^1$ is hydrogen or C$_1$–C$_6$-alkyl optionally substituted with aryl or heteroaryl;
B is absent or is selected from the group consisting of
  (1) —(CH$_2$)$_q$—, wherein q is 0, 1, 2, 3, 4, 5, or 6,
  (2) —C(O)—(CH$_2$)$_q$—,
  (3) —C(O)—O—(CH$_2$)$_q$—,
  (4) —C(O)—NR$^1$—(CH$_2$)$_q$—, wherein R$^1$ is as defined previously, and
  (5) —N═CH—(CH$_2$)$_q$—;
  (6) —CH(OH)—(CH$_2$)$_q$—, and
  (7) —CH(OH)—CH(OH)—(CH$_2$)$_q$—;
D is absent or is selected from the group consisting of
  (1) alkenylene,
  (2) arylene,
  (3) substituted arylene,
  (4) heteroarylene,
  (5) substituted heteroarylene;
  (6) alkenylene-arylene,
  (7) arylene-arylene,
  (8) substituted arylene-arylene,
  (9) heteroarylene-arylene,
  (10) substituted heteroarylene-arylene,
  (11) alkenylene-heteroarylene,
  (12) arylene-heteroarylene,
  (13) substituted arylene-heteroarylene,

(14) heteroarylene-heteroarylene, and
(15) substituted heteroarylene-heteroarylene;

E is absent or is selected from the group consisting of
(1) —(CH$_2$)$_r$—CH=CH—,
(2) —(CH$_2$)$_r$—O—, wherein r is 0, 1, 2, 3 or 4,
(3) —(CH$_2$)$_r$—NR$^1$—CH$_2$—CH(OH)—, wherein R$^1$ is as defined previously,
(4) —(CH$_2$)$_r$—C(O)—O—,
(5) —(CH$_2$)$_r$—N(R$^1$)—,
(6) —(CH$_2$)$_r$—O—C(O)—,
(7) —(CH$_2$)$_r$—C(O)—N(R$^1$)—, and
(8) —(CH$_2$)$_r$—N(R$^1$)—C(O)—, with the restrictions that the sum of m+q may not be 0, that the sum of m+n+q+r is an integer from 2 to 7, that when the A and B moieties are both absent then m cannot be 0, that when E is —CH=CH— and the A, B and D moieties are all absent then m cannot be 0, and that B can be —N=CH—(CH$_2$)$_q$— only when A is absent and m is 0, the method comprising (a) treating a compound having the formula

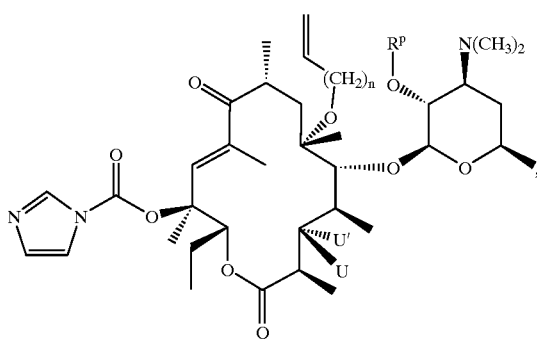

wherein U is 4"-R$^P$-O-cladinose and U' is H, or U and U' taken together with the carbon atom to which they are attached form a carbonyl group, with a first reagent compound having the formula H$_2$N—(CH$_2$)$_m$—A—X$^2$, wherein m and A are as defined previously and X$^2$ is H, to prepare an intermediate compound having the formula

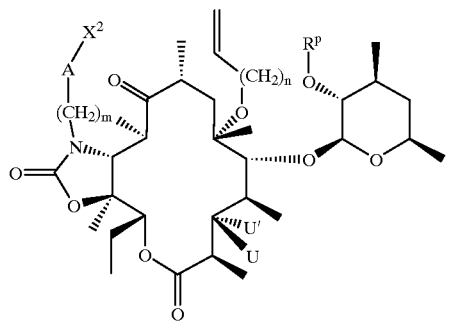

(b) treating the intermediate compound from Step (a) with a reagent compound having the formula B'—D—X$^1$, wherein X$^1$ is a leaving group selected from the group consisting of Cl, Br, I and trifluoromethanesulfonate, B' is a B-precursor moiety, and D is as defined previously, to prepare a second intermediate compound having the formula

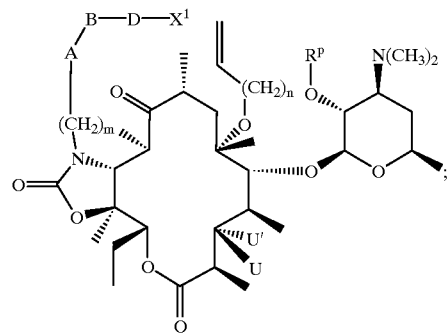

and (b) cyclizing and optionally reducing the compound from Step (b).

14. The process of claim 13 wherein U is 4"-R$^P$-O-cladinose, and the product is a compound of formula (I).

15. The process of claim 14, wherein the reagent of Step (a) having the formula H$_2$N—(CH$_2$)$_m$—A—X$^2$ is selected from the group consisting of hydrazine and ethylenediamine.

16. A process for preparing a compound selected from the group consisting of

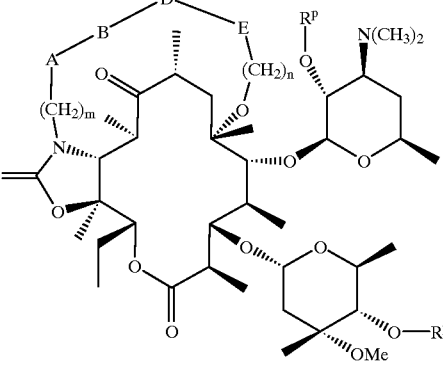

and

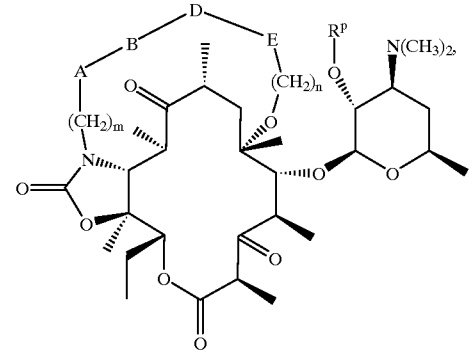

wherein
m is 0, 1, 2, 3, 4, 5, 6 or 7;
n is 0, 1, 2, 3 or 4;
R$^P$ is independently hydrogen or a hydroxy protecting group at each occurrence;
A is absent or is selected from the group consisting of
(1) —O—, and
(2) —N(R$^1$)—, wherein R$^1$ is hydrogen or C$_1$–C$_6$-alkyl optionally substituted with aryl or heteroaryl;

B is absent or is selected from the group consisting of
(1) —(CH$_2$)$_q$—, wherein q is 0, 1, 2, 3, 4, 5, or 6,
(2) —C(O)—(CH$_2$)$_q$—,
(3) —C(O)—O—(CH$_2$)$_q$—,
(4) —C(O)—NR$^1$—(CH$_2$)$_q$—, wherein R$^1$ is as defined previously, and
(5) —N=CH—(CH$_2$)$_q$—;
(6) —CH(OH)—(CH$_2$)$_q$—, and
(7) —CH(OH)—CH(OH)—(CH$_2$)$_q$—;

D is absent or is selected from the group consisting of
(1) alkenylene,
(2) arylene,
(3) substituted arylene,
(4) heteroarylene,
(5) substituted heteroarylene;
(6) alkenylene-arylene,
(7) arylene-arylene,
(8) substituted arylene-arylene,
(9) heteroarylene-arylene,
(10) substituted heteroarylene-arylene,
(11) alkenylene-heteroarylene,
(12) arylene-heteroarylene,
(13) substituted arylene-heteroarylene,
(14) heteroarylene-heteroarylene, and
(15) substituted heteroarylene-heteroarylene;

E is absent or is selected from the group consisting of
(1) —(CH$_2$)$_r$—CH=CH—,
(2) —(CH$_2$)$_r$—O—, wherein r is 0, 1, 2, 3 or 4,
(3) —(CH$_2$)$_r$—NR$^1$—CH$_2$—CH(OH)—, wherein R$^1$ is as defined previously,
(4) —(CH$_2$)$_r$—C(O)—O—,
(5) —(CH$_2$)$_r$—N(R$^1$)—,
(6) —(CH$_2$)$_r$—O—C(O)—,
(7) —(CH$_2$)$_r$—C(O)—N(R$^1$)—, and
(8) —(CH$_2$)$_r$N(R$^1$)—C(O)—, with the restrictions that the sum of m +q may not be 0, that the sum of m+n+q+r is an integer from 2 to 7, that when the A and B moieties are both absent then m cannot be 0, that when E is —CH=CH— and the A, B and D moieties are all absent then m cannot be 0, and that B can be —N=CH—(CH$_2$)$_q$— only when A is absent and m is 0, the method comprising
(a) treating a compound having the formula

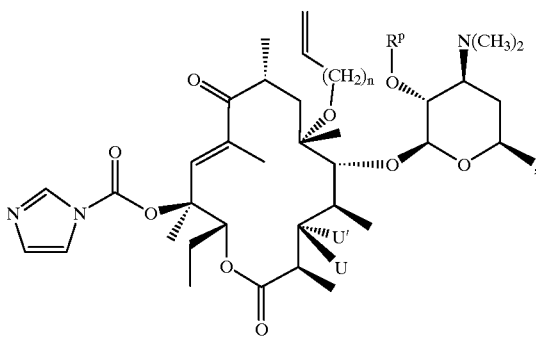

wherein U is 4"-R$^p$-O-cladinose and U' is H, or U and U' taken together with the carbon atom to which they are attached form a carbonyl group, with a first reagent compound having the formula H$_2$N—(CH$_2$)$_m$—A—X$^2$, wherein m and A are as defined previously and X$^2$ is a N-protecting group, to prepare an intermediate compound having the formula

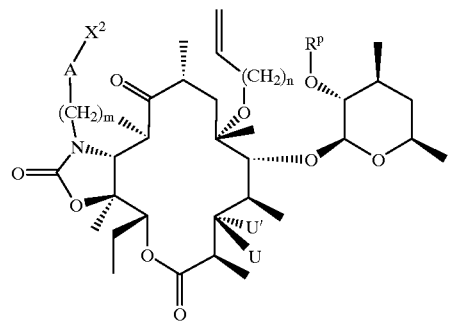

(b) treating the intermediate compound from Step (a) with a reagent compound having the formula B'—D—X$^1$, wherein X$^1$ is a leaving group selected from the group consisting of Cl, Br, I and trifluoromethanesulfonate, B' is a B-precursor moiety, and D is as defined previously, to prepare an second intermediate compound having the formula

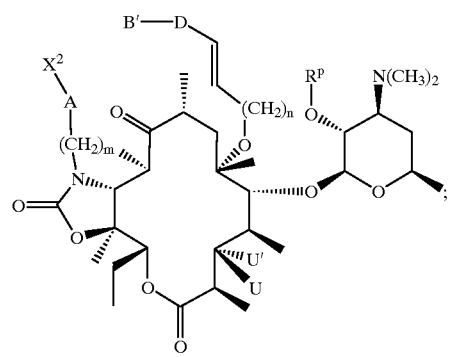

and (b) cyclizing and optionally reducing the compound from Step (b).

17. The process of claim 16 wherein U is 4"-R$^p$-O-cladinose, and the product is a compound of formula (I).

18. A process for preparing a compound selected from the group consisting of (I)

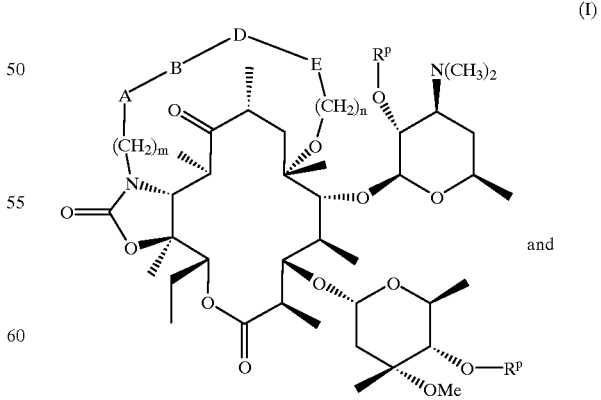

and

-continued (II)

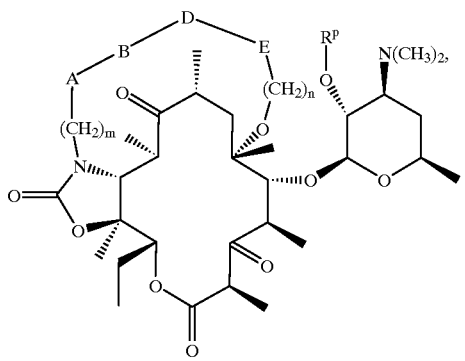

wherein
m is 0, 1, 2, 3, 4, 5, 6 or 7;
n is 0, 1, 2, 3 or 4;
$R^p$ is independently hydrogen or a hydroxy protecting group at each occurrence;
A is absent or is selected from the group consisting of
(1) —O—, and
(2) —N($R^1$)—, wherein $R^1$ is hydrogen or $C_1$–$C_6$-alkyl optionally substituted with aryl or heteroaryl;
B is absent or is selected from the group consisting of
(1) —(CH$_2$)$_q$—, wherein q is 0, 1, 2, 3, 4, 5, or 6,
(2) —C(O)—(CH$_2$)$_q$—,
(3) —C(O)—O—(CH$_2$)$_q$—,
(4) —C(O)—NR$^1$—(CH$_2$)$_q$—, wherein $R^1$ is as defined previously, and
(5) —N═CH—(CH$_2$)$_q$—;
(6) —CH(OH)—(CH$_2$)$_q$—, and
(7) —CH(OH)—CH(OH)—(CH$_2$)$_q$—;
D is absent or is selected from the group consisting of
(1) alkenylene,
(2) arylene,
(3) substituted arylene,
(4) heteroarylene,
(5) substituted heteroarylene;
(6) alkenylene-arylene,
(7) arylene-arylene,
(8) substituted arylene-arylene,
(9) heteroarylene-arylene,
(10) substituted heteroarylene-arylene,
(11) alkenylene-heteroarylene,
(12) arylene-heteroarylene,
(13) substituted arylene-heteroarylene,
(14) heteroarylene-heteroarylene, and
(15) substituted heteroarylene-heteroarylene;
E is absent or is selected from the group consisting of
(1) —(CH$_2$)$_r$—CH═CH—,
(2) —(CH$_2$)$_r$—O—, wherein r is 0, 1, 2, 3 or 4,
(3) —(CH$_2$)$_r$—NR$^1$—CH$_2$—CH(OH)—, wherein $R^1$ is as defined previously,
(4) —(CH$_2$)$_r$—C(O)—O—,
(5) —(CH$_2$)$_r$—N(R$^1$)—,
(6) —(CH$_2$)$_r$—O—C(O)—,
(7) —(CH$_2$)$_r$—C(O)—N(R$^1$)—, and
(8) —(CH$_2$)$_r$—N(R$^1$)—C(O)—,
with the restrictions that the sum of m+q may not be 0, that the sum of m+n+q+r is an integer from 2 to 7, that when the A and B moieties are both absent then m cannot be 0, that when E is —CH═CH— and the A, B and D moieties are all absent then m cannot be 0, and that B can be —N═CH—(CH$_2$)$_q$— only when A is absent and m is 0, the method comprising
(a) treating a compound having the formula

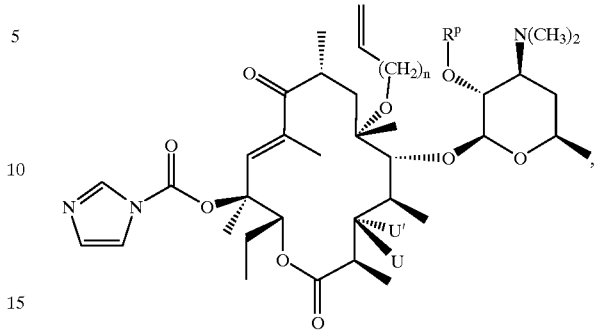

wherein U is 4"-$R^p$-O-cladinose, $R^p$ is a hydroxy protecting group, and U' is H, or U and U' taken together with the carbon atom to which they are attached form a carbonyl group, with a first reagent compound having the formula $H_2N$—(CH$_2$)$_m$—A—B—D—X$^3$, wherein m, A, B, D are as defined previously and X$^3$ is —(CH$_2$)$_r$—Y, wherein r is as defined previously and Y is a N-precursor, an acyl-precursor, hydroxyl or —CH$_2$—I moiety, to prepare a first intermediate compound having the formula

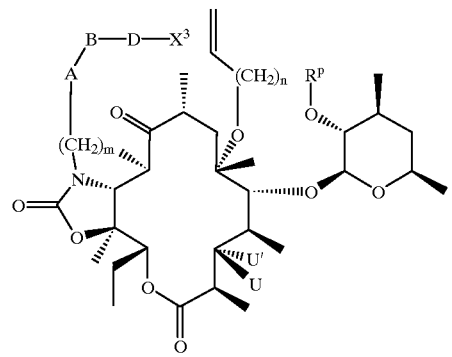

(b) treating the first intermediate compound from Step (a) with double bond modifying reagents, to prepare an second intermediate compound having the formula

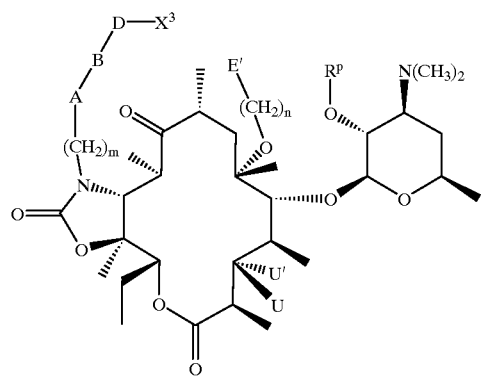

wherein E' is an E-precursor having a reactive moiety selected from the group consisting of —CH(O), —OH, —NH$_2$, —C(O)OH, and an epoxy ring; and
(c) cyclizing the compound from Step (b).

19. The process of claim 18 wherein U is 4"-$R^p$-O-cladinose, and the product is a compound of formula (I).

* * * * *